United States Patent [19]
Staehelin et al.

[11] Patent Number: 5,935,822
[45] Date of Patent: Aug. 10, 1999

[54] PRODUCT AND PROCESS FOR MEMBRANE AND SOLUBLE POLYPEPTIDE SEGREGATION

[75] Inventors: Andrew Staehelin, Boulder, Colo.; David Galbraith, Tucson, Ariz.; Thomas Giddings, Longmont, Colo.

[73] Assignee: The Regents of the University Of Colorado, Boulder, Colo.

[21] Appl. No.: 08/407,900

[22] Filed: Mar. 21, 1995

[51] Int. Cl.$^6$ ............ C12P 21/02; C12N 1/100; C12N 5/10; C12N 15/11
[52] U.S. Cl. ............ 435/69.7; 435/325; 435/375; 435/410; 536/23.4
[58] Field of Search ............ 435/69.7, 325, 435/243, 410, 375; 536/23.4

[56] References Cited

U.S. PATENT DOCUMENTS

| | | | |
|---|---|---|---|
| 5,268,463 | 12/1993 | Jefferson | 536/237 |
| 5,270,181 | 12/1993 | McCoy et al. | 435/69.7 |

OTHER PUBLICATIONS

Denecke et al., 1990, *Plant Cell*, vol. 2, pp. 51–59.
Iturriaga et al., 1989, *Plant Cell*, vol. 1, pp. 381–390.
Koning et al., 1993, *Cell Motility and the Cytoskeleton*, vol. 25, pp. 111–128.
Pang et al., 1992, *Gene*, vol. 112, pp. 229–234.
Wright et al., 1988, *J. Cell Biol.*, vol. 107, pp. 101–114.
Wright el al., 1990, *The New Biologist*, vol. 2, No. 10, pp. 915–921.
Wright et al., 1989, *Methods Cell Biol.*, vol. 31, pp. 473–512.

*Primary Examiner*—Terry McKelvey
*Attorney, Agent, or Firm*—Sheridan Ross P.C.

[57] ABSTRACT

The present invention relates to a novel product and process for segregating desired product molecules within a cell. Aggregate molecules comprising an adhesive molecule attached to a desired product molecule, are sequestered in or in association with a portion of a lipid bilayer in a protective manner. The invention is additionally directed to methods to nucleic acid molecules, recombinant cells, delivery vehicles, secretion systems, assays for identifying proteins capable of associating with another protein and biological sensing systems, such embodiments having a variety of therapeutic, diagnostic, biosynthetic production, agricultural, bioremediation and forestry uses.

50 Claims, 5 Drawing Sheets

```
                              SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 1..33
          (D) OTHER INFORMATION: /label= primer (xi) SEQUENCE DESCRIPTION: SEQ ID NO:1:

GCGCGTCGAC CGACCATGTC CAAGGAGACA AAT                                   33

(2) INFORMATION FOR SEQ ID NO:2:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 1..27
          (D) OTHER INFORMATION: /label= primer (xi) SEQUENCE DESCRIPTION: SEQ ID NO:2:

GGCCCCCATG GTGTAAAGAC TACTTCC                                          27

(2) INFORMATION FOR SEQ ID NO:3:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 1..30
          (D) OTHER INFORMATION: /label= primer
```

(xi) SEQUENCE DESCRIPTION: SEQ ID NO:3:

GGCCCCCATG GTATAAATAA CCTTACTTCT                                                  30

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..29
        (D) OTHER INFORMATION: /label= primer (xi) SEQUENCE DESCRIPTION: SEQ ID NO:4:

CCCTCGAGAT GTCTCATATA ATGAACCTT                                                   29

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..26
        (D) OTHER INFORMATION: /label= primer (xi) SEQUENCE DESCRIPTION: SEQ ID NO:5:

GGGGTACCTT CAGATGTCGT TCAGAA                                                      26

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Lys Asp Glu Leu
    1

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

His Asp Glu Leu
    1

(2) INFORMATION FOR SEQ ID NO:8:

```
        (i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:8:

Arg Gly Asp Leu
    1

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:9:

Lys Lys Xaa Xaa
    1

(2) INFORMATION FOR SEQ ID NO:10:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:10:

Lys Xaa Lys Xaa Xaa
    1               5

(2) INFORMATION FOR SEQ ID NO:11:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:11:

Arg Lys Pro Arg Arg Glu
    1               5

(2) INFORMATION FOR SEQ ID NO:12:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO:12:

Arg Arg Xaa Xaa
```

PRODUCT AND PROCESS FOR MEMBRANE AND SOLUBLE POLYPEPTIDE SEGREGATION

This invention was made in part with government support under: NSF MCB-92-05451, awarded by the National Science Foundation; USDA Hatch ARZT-136544-H-25-131, awarded by the U.S. Department of Agriculture; and NIH GM-18639 Grant AI 22295, awarded by the National Institutes of Health. The government has certain rights to this invention.

FIELD OF THE INVENTION

The present invention is related to a novel process for accumulating and producing desired product molecules. More particularly, the present invention includes a process for accumulating chimeric molecules capable of forming oligomers in or within a portion of a lipid bilayer or the cytoplasm.

BACKGROUND OF THE INVENTION

General limitations on commercial production of compounds include the efficiency of synthesis and, if a complex synthesis process is involved, the efficiency of recovery. Polypeptide production is an example of the limitations that can effect commercial production. The advent of recombinant DNA techniques has enabled investigators to produce substantial amounts of desired polypeptides in a variety of expression systems (e.g., bacterial, fungal, mammalian, yeast, plant and insect cells). Several problems typically occur, however, when such cell types are used as host cells for heterologous gene expression. For example, recombinant polypeptides produced by expression of heterologous genes in eukaryotic cells are often rapidly degraded by proteases in the cells. Those polypeptides that do manage to accumulate when expressed in a cell can be disruptive to the normal machinery of the cell, thereby lowering the growth and/or survival rate and the polypeptide production ability of the cell.

Recombinant polypeptides produced by expression of heterologous genes in bacterial cells are usually found in the insoluble or "inclusion body" fraction of a bacterial lysate, rendering the bacterial cells and the polypeptides useless for biological and biochemical applications. Such inclusion bodies typically require further manipulation in order to solubilize and re-fold the recombinant polypeptide under conditions that must be determined empirically, resulting in further uncertainties. Moreover, recombinant polypeptides produced in bacterial cells often have low activity due to a failure of the polypeptides to assume a natural conformation and/or the inability of cells to glycosylate such polypeptides.

To overcome these problems, prior investigators have concentrated on improving the expression of recombinant polypeptides in bacterial cells using various "fusion partners" linked to desired heterologous polypeptides to enable the expression and/or secretion of polypeptides in large amounts (U.S. Pat. No. 5,270,181, by McCoy et al., issued Dec. 14, 1993). Such fusion protein systems, however, fail to overcome the basic protein conformation problems encountered by expressing heterologous genes in a bacterial cell.

The use and purification of polypeptides produced by recombinant expression systems is a serious problem since recombinant production of polypeptides has become a mainstay in the development and production of therapeutic and diagnostic reagents. There is a continuing need for a simpler and commercially efficient method to produce substantial amounts of optimally active recombinant polypeptides for use in experimental, therapeutic and diagnostic applications.

SUMMARY OF THE INVENTION

General limitations in the commercial production of compounds (e.g., polypeptides) include problems relating to the efficiency of synthesis and, if a complex synthesis process is involved, the efficiency of recovery. The present invention provides a simpler and commercially efficient method to produce substantial amounts of a desired product molecule. The present invention provides a product and process for aggregating desired product molecules such that the desired molecules are sequestered in or within lipid bilayers. Such sequestration acts to protect the integrity of a product molecule, as well as to facilitate recovery of the molecule. In addition to the production and recovery of a desired product molecule, the novel sequestration method of the present invention can be used in a variety of applications. For example, a therapeutic composition can be produced by aggregating a desired product molecule in a plant cell, and the plant cell can be fed to an animal to administer the composition. Further uses of the present invention are described in detail below.

One aspect of the present invention includes a method to aggregate a desired product molecule in a lipid bilayer, comprising forming oligomers between two or more aggregate molecules that are physically associated with a lipid bilayer such that the aggregate molecules are accumulated while in association with the lipid bilayer. The accumulation of the aggregate molecules generates at least one membrane compartment having a morphology substantially similar to one or more membrane compartments shown in FIG. 4. Preferably the present method is performed in vivo and the steps of synthesis, aggregation and sequestration do not substantially interfere with cellular function.

Another aspect of the present invention includes a non-naturally occurring membrane housing compartment, comprising an intracellular structure inside of which proteins are sequestered without substantially interfering with cellular function. Preferred membrane housing compartments include stacked membrane structures and planar membrane structures. More preferred membrane housing compartments are formed by forming oligomers between a sufficient number of aggregate molecules such that a membrane compartment is formed that is substantially similar to the morphology of one or more membrane compartments shown in FIG. 4.

Yet another aspect of the present invention includes a nucleic acid molecule encoding an aggregate molecule comprising: a) an adhesive molecule capable of forming oligomers between two or more aggregate molecules, the adhesive molecule to a lipid bilayer; and b) a desired product molecule functionally associated with the adhesive molecule. A preferred nucleic acid molecule encodes at least a portion of β-glucuronidase that is capable of forming an oligomer with another molecule. A more preferred nucleic acid molecule further comprises a nucleic acid sequence that encodes a transmembrane molecule comprising at least a portion of a coronavirus avian infectious bronchitis virus M protein. Also included in the present invention is a recombinant cell having a recombinant molecule comprising a nucleic acid molecule of the present invention operatively linked to an expression vector.

One embodiment of the present invention comprises a delivery vehicle comprising a recombinant cell having at least one nucleic acid molecule encoding a reagent and an aggregate molecule, the aggregate molecule being capable of physically associating with a lipid bilayer. The reagent can be chosen from antigens, toleragens, drugs (e.g., antibiotics or anti-neoplastic drugs), toxic compounds, markers, hormones, antibodies, cytokines and growth factors.

Another embodiment of the present invention includes a command secretion system, comprising: a) a recombinant cell comprising: (i) a nucleic acid molecule encoding an aggregate molecule comprising an adhesive molecule and a desired product molecule, in which the desired product molecule is linked to the adhesive molecule by a transmembrane molecule, the desired product molecule being covalently attached to a proteolytic restriction site; (ii) a nucleic acid molecule encoding a protease that is capable of cleaving the desired product molecule from the transmembrane molecule at the proteolytic restriction site; and b) an inducing agent capable of inducing the expression of the nucleic acid molecule encoding the protease.

Yet another embodiment of the present invention includes an assay for identifying protein associated molecules, comprising: a) forming a sequestered protein complex by contacting a first adhesive molecule attached to a first subunit of a protein formation, with a second adhesive molecule attached to a second subunit of the protein formation; b) contacting the sequestered protein complex with a putative associated molecule; and c) determining whether the putative associated molecule is capable of associating with the sequestered protein complex by assessing the binding of the putative associated molecule to the sequestered protein complex. Preferably, the first subunit is identical to the second subunit.

The present invention also includes a biological sensor system formed by the method comprising aggregating aggregate molecules that are physically associated with a lipid bilayer in such a manner that the aggregate molecules are accumulated in association with a portion of the lipid bilayer, the aggregate molecules being functionally associated with a biological sensing molecule. Preferably, the biological sensing molecule comprises a molecule capable of responding to a stimulus such as light or chemicals.

Another aspect of the present invention comprises a method to detoxify a cell, comprising: a) providing to a cell an adhesive molecule having at least one site capable of binding to a free-floating toxin; and b) contacting the adhesive molecule with the toxin, whereby said adhesive molecule and toxin form a complex that is less toxic to the cell than the free-floating toxin.

Yet another aspect of the present invention comprises a method for increasing the concentration of a desired product molecule within a cell, comprising: a) forming within a cell oligomers between two or more aggregate molecules having desired product molecules attached thereto, wherein the concentration of the desired product molecules in the cell exceeds the concentration of the desired product molecules in cells where the oligomers are not formed.

DETAILED DESCRIPTION OF THE INVENTION

Figure 1:
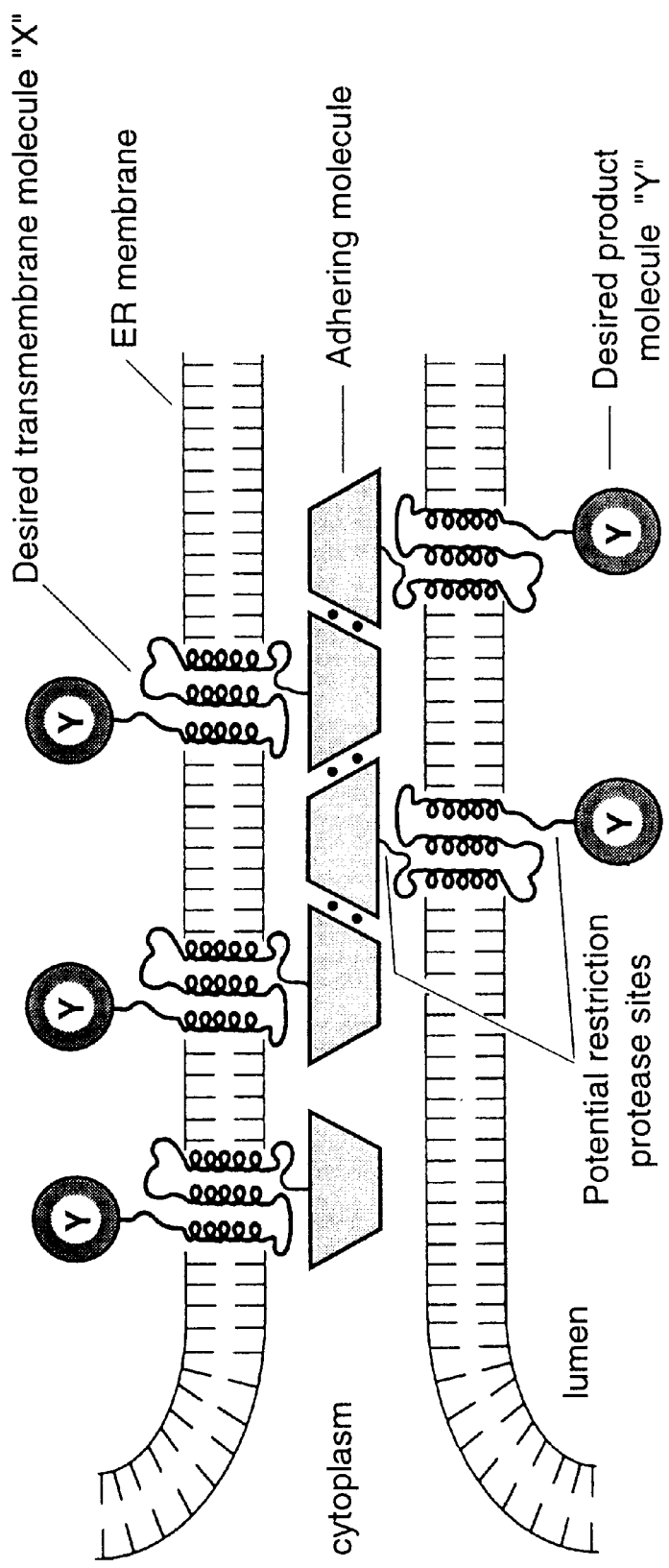
FIG. 1 schematically illustrates the interaction of aggregating molecules attached to a lipid bilayer on the cytoplasmic side of an organelle membrane.
Figure 2:
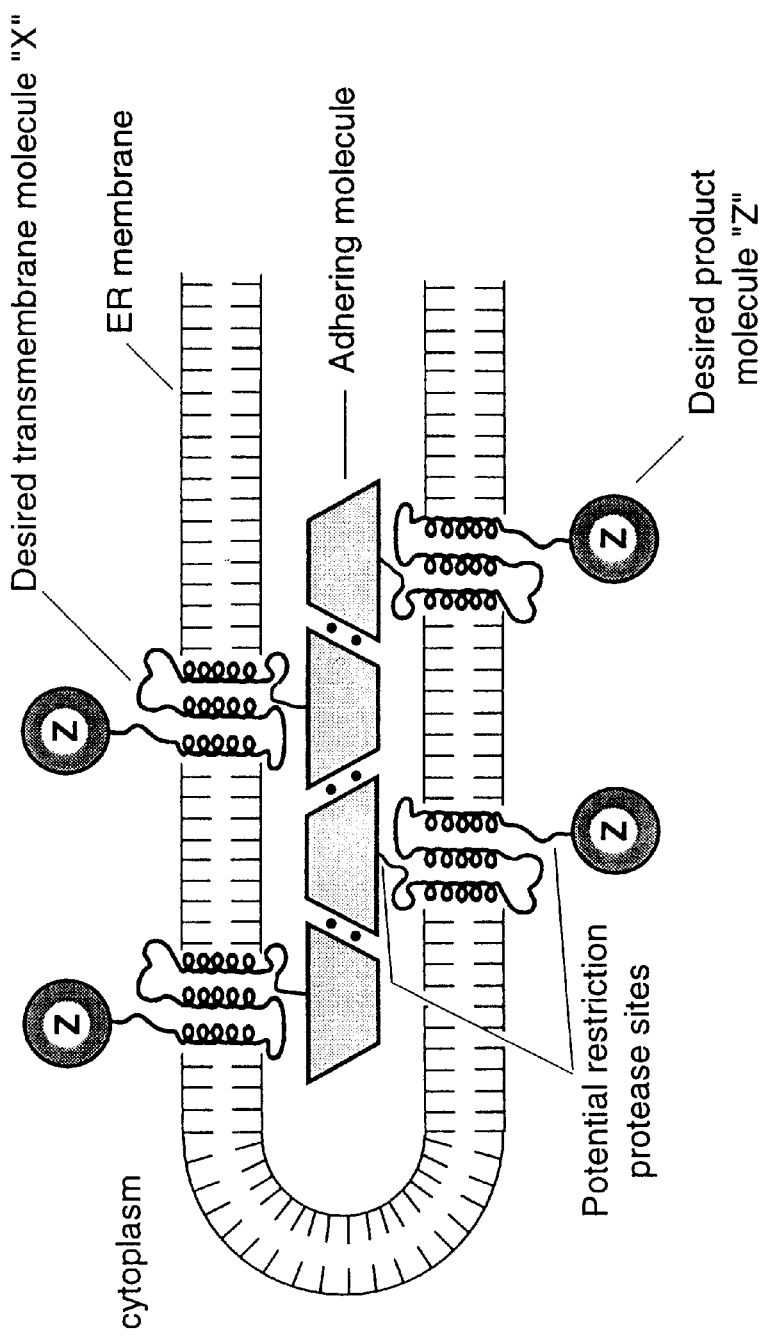
FIG. 2 schematically illustrates the interaction of aggregating molecules attached to a lipid bilayer on the lumenal side of an organelle membrane.
Figure 3:
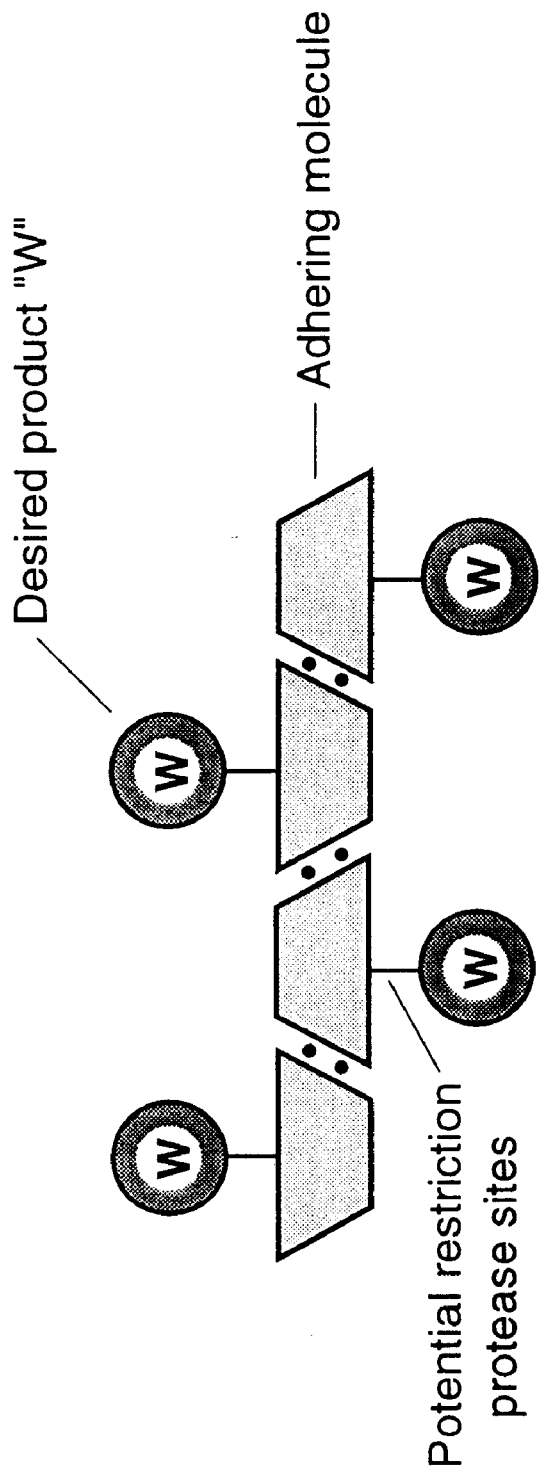
FIG. 3 schematically illustrates the interaction of aggregating molecules not attached to a lipid bilayer.
Figure 4:
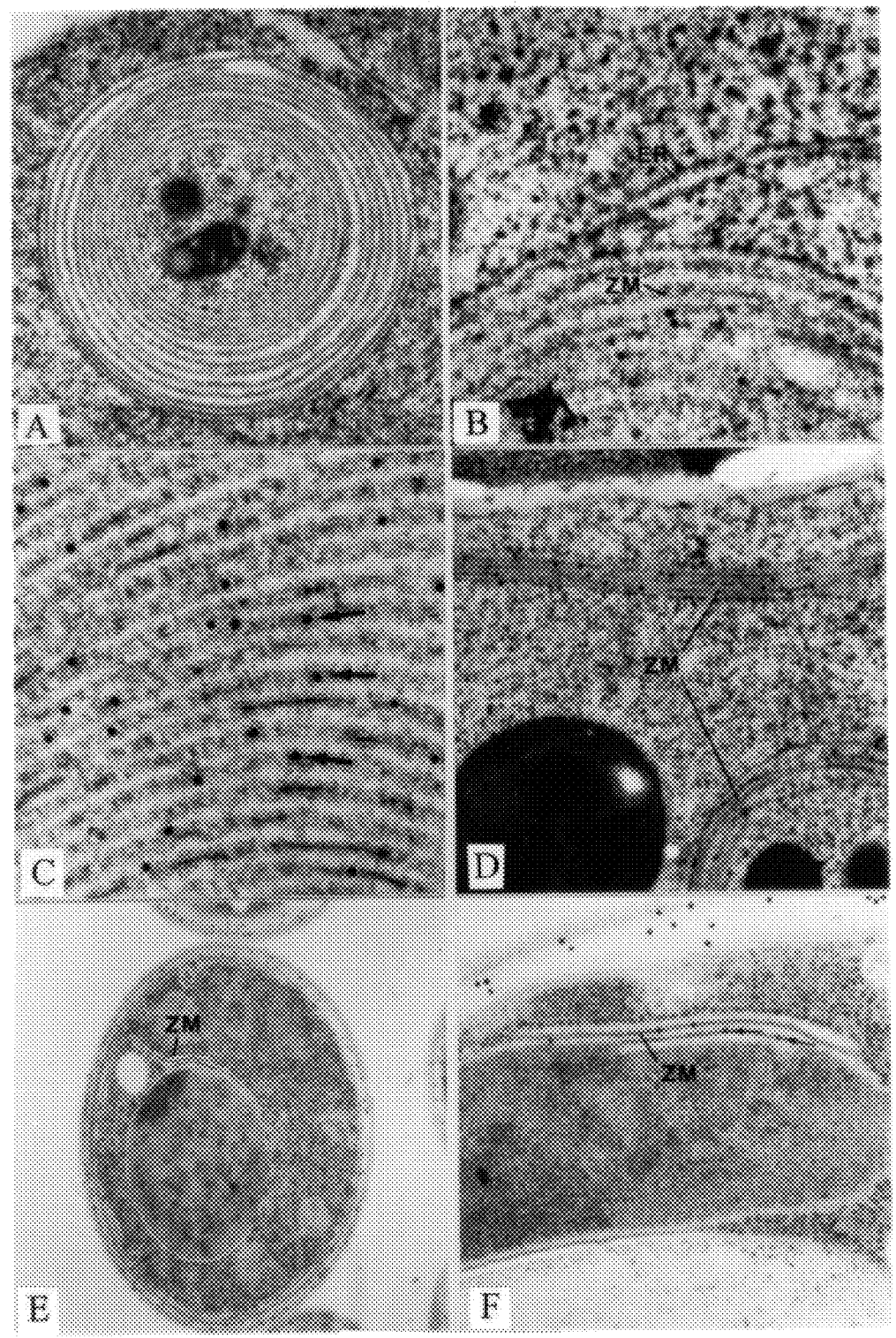
FIG. 4A is an electron micrograph of a Zippered-membrane (Z-membrane) whorl formed in a tobacco plant cell.
FIG. 4B is an electron micrograph of forming Z-membrane whorls in which the zippering of adjacent ER membranes is seen.
FIG. 4C is an electron micrograph of Z-membranes formed in a tobacco cell and immunolabelled with antibodies specific for GUS.
FIG. 4D is an electron micrograph of a tobacco cell in which both stacked and whorled Z-membranes are seen.
FIG. 4E is an electron micrograph of Z-membranes formed in a yeast cell.
FIG. 4F is an electron micrograph of a yeast cell with stacked Z-membranes immunolabelled with antibodies specific for GUS.

The present invention generally relates to a novel process for producing a desired product molecule. The present invention includes a novel aggregating molecule (AgM) having at least two components: (1) an adhesive molecule (AdM) capable of forming oligomers with other AdM's such that the AdM's are accumulated within or in a portion of a membrane; and (2) a desired product molecule (DPM). An AdM can be linked to a desired transmembrane molecule (DTm) capable of securing the AgM in a lipid bilayer in such a manner that the DTm remains attached to the lipid bilayer during oligomer formation between the AdM's (schematically illustrated in FIGS. 1 and 2). An AdM can also be free-floating (i.e., not membrane-bound) as schematically illustrated in FIG. 3.

The invention is particularly advantageous in that it permits the production of substantial amounts of desired compounds, for example, heterologous molecules such as polypeptides, in a variety of cell types that normally express only limited amounts of such compounds. Novel AgMs of the present invention are capable of forming oligomers that are sequestered in and/or within a portion of a membrane. As used herein, the term "membrane" refers to a structure comprising a lipid bilayer that may contain macromolecules, such as proteins and other lipid molecules. The term "within a portion of a membrane" refers to an aggregate molecule that is surrounded by a lipid bilayer (i.e., in the lumen surrounded by a lipid bilayer but not anchored in the lipid bilayer), while the term "in a membrane" refers to an AgM that spans a portion of a lipid bilayer. If performed in vivo, such sequestration can essentially prevent the degradation of the AgMs by cellular proteases, as well as allow the accumulation of AgMs in a manner that does not significantly interfere with the normal function of the cell. AgMs capable of being sequestered in and/or within a portion of a membrane include AdMs covalently attached or functionally associated with DPMs by a desired transmembrane molecule, both described in detail below.

The inefficiency and unpredictable integrity of recombinantly produced molecules limits the use of recombinant nucleic acid technology for commercial production of desired reagents for therapeutic, diagnostic and/or experimental use. Using the novel AdM of the present invention allows for the accumulation without degradation of a recombinantly produced heterologous molecule in or within a portion of a membrane. The ability to accumulate a recombinantly produced heterologous molecule in or within a portion of a cellular membrane is unexpected because such accumulation typically disrupts normal cellular function by interfering with normal protein production by a cell. As such, a skilled artisan would predict that accumulation of recombinantly produced heterologous molecules would lead to cell death. Despite such predictions, the present inventors have identified and produced AdMs that localize recombinantly produced molecules in or within a portion of a cell membrane without interfering with the functioning of normal housekeeping proteins of the cell.

An AdM of the present invention can comprise a molecule that is capable of forming lateral oligomers, apposing oligomers and/or lateral/apposing oligomers. As used herein, the term "oligomer" refers to a composition comprising two or more AdMs associated in a specific and stable manner under biological conditions. Such AdMs can be associated by, for example, covalent linkage, peptide bonding, polar interactions, di-sulfide bonds, salt bridges, hydrogen bonds, hydrophobic interactions, or Van Der Waals forces. A first AdM may be capable of associating with a second AdM in more than one way. For instance, lateral oligomers refer to the side-by-side association of two or more "sided" AdMs. Apposing oligomers refer to the head-to-head association of two or more "sided" AdMs. Lateral/apposing oligomers refers to the combined side-by-side and head-to-head association of two or more "sided" AdMs.

Preferred AdMs of the present invention include at least a portion of a polypeptide capable of forming homo-oligomers or hetero-oligomers (referred to herein as an adhesive polypeptide), a lectin, a receptor, a receptor ligand, and other specific protein and non-protein interactions such as avidin/biotin. As used herein, a "polypeptide" refers to an amino acid sequence which, upon hydrolysis, yields more than two amino acids and more preferably at least about five amino acids. Suitable adhesive polypeptides of the present invention comprise any amino acid sequence that is capable of allowing oligomer formation. Preferably, the size of an adhesive polypeptide of the present invention is between about 0.5 kD and about 200 kD, more preferably between about 5 kD and about 100 kD, and even more preferably between about 5 kD and about 75 kD, or about 73 kD.

In addition, the amino acid composition of an adhesive polypeptide of the present invention is preferably charged such that a first adhesive polypeptide can stably associate with a second adhesive polypeptide. Any combination of positively and negatively charged amino acids that enable two or more adhesive polypeptides to stably associate are suitable for the present invention. For example, a first adhesive polypeptide comprises a stretch of five or more negatively charged amino acid residues that are capable of associating with a stretch of five or more positively charged amino acid residues contained in a second adhesive polypeptide. Alternatively, at least a portion of a first adhesive polypeptide can comprise a stretch of hydrophobic amino acid residues flanked by hydrophilic amino acid residues, in which the hydrophobic residues associate with a stretch of hydrophobic amino acid residues on a second adhesive polypeptide.

Preferred adhesive polypeptides of the present invention include, but are not limited to, β-glucuronidase; ribulose-1-5-bisphosphate carboxylase; hemoglobin; viral envelope proteins derived from viruses such as orthomyxoviruses, paramyxoviruses, rhabdoviruses, herpesviruses, hepadnaviruses and lentiviruses. Other suitable viral proteins that can serve as AdMs include, but are not limited to, T4 phage coat protein and T4 phage tail protein. Suitable lectins include, but are not limited to, concanavalin A and hemagglutinin. Suitable receptors that can serve as ADMs include, but are not limited to immunoglobulin, LDL receptor, epidermal growth factor receptor and platelet-derived growth factor receptor. Suitable ligands include, but are not limited to antigen, LDL. epidermal growth factor and platelet growth factor. Other suitable non-protein and protein interactions include biotin and avidin. It is within the scope of the present invention to use more than one pair of AdMs to form desired structures.

It is within the scope of the present invention that hybrids of any of the foregoing molecules can be used as an AdM of the present invention. As used herein, a "hybrid" refers to the attachment of at least a portion of a first AdM to at least a portion of a second different AdM. According to the present invention, "at least a portion of an AdM" refers to a portion of an AdM capable of forming an oligomer with another AdM. A particularly preferred AdM of the present invention includes at least a portion of β-glucuronidase protein.

A DPM of the present invention includes any molecule that is desirable to accumulate in or in association with a portion of a membrane, and that is capable of being linked to an AdM of the present invention. As such, a DPM can include any molecule that one wishes to: produce and recover; deliver to a cell; or localize in a region of a cell or a membrane. A DPM, thus includes protein-based compounds, carbohydrate-based compounds, lipid-based compounds, vitamins, synthetic chemical compounds, metal binding compounds and nucleic acids. In one embodiment, a DPM of the present invention is a protein, and more preferably a protein that can be recombinantly produced. A desired product protein can be a secreted protein or an intracellular protein. Particularly preferred desired product proteins include, but are not limited to, at least a portion of a viral envelope protein, an enzyme that regulates lipid production, an enzyme that regulates steroid production, an enzyme that degrades a substance toxic to a cell, an enzyme that degrades plant cell walls, an anti-thrombin molecule, an antigen, a toleragen, a cytokine, a toxin, enzymes whose absence is associated with a disease and enzymes that are not toxic to an animal until released from an AgM of the present invention (e.g., released in the gut of an animal. A toxin suitable for use as a DPM includes a molecule that is toxic to an animal pathogen (e.g., bacteria, fungi, insects and parasites) but not to the animal. Association of such a toxin to an adhesive molecule of the present invention enables one to deliver the aggregate molecule containing the toxin to animal (i.e., through the gut by feeding the aggregate molecule to the animal) to destroy the pathogen without harming the animal.

In one embodiment, a DPM of the present invention comprises a desired transmembrane molecule (DTm), preferably one that is capable of physically associating an AdM of the present invention with a lipid bilayer. The term "physically associating" refers to the securing of an AdM to a lipid bilayer in such a manner that the AdM remains secured to the membrane during oligomer formation (i.e., during the aggregation step in accordance with the method of the present invention) between two AdMs. The physical association of an AdM with a membrane must be sufficiently stable to preserve the association for a desired period of time, preferably between about 1 hour and 3 weeks, more preferably between about 3 hours and 2 weeks, and even more preferably between about 6 hours and 1 week.

Conversely, the physical association of an AdM with a membrane is preferably sufficiently unstable to allow the dissociation and subsequent recovery of a transmembrane molecule from the membrane using standard recovery techniques, such as centrifugation, detergent solubilization and chromatography. Such standard techniques include disrupting a cell prior to recovery of the transmembrane molecule by, for example, sonication, grinding (with or without beads), osmotic shock or French press. The physical association of an AdM with a membrane should be sufficiently unstable to allow dissociation of the AdM from a lipid bilayer after exposure of the lipid bilayer to between about 0.1% and about 1%, and more preferably about 2% sodium dodecyl sulfate (SDS) for about 1 hour.

A preferred DTm of the present invention comprises a transmembrane region of a protein that is capable of securing an AdM by extending partially or completely through a lipid bilayer. A preferred transmembrane region extends through both layers of a lipid bilayer. A transmembrane region of the present invention may also comprise more than one membrane-spanning domain, preferably comprising between about 1 and about 12 membrane-spanning domains, more preferably between about 1 and about 6 membrane-spanning domains, and even more preferably about 3 membrane-spanning domains.

A transmembrane region of the present invention can be selected from any protein capable of inserting into a lipid bilayer (i.e., a transmembrane protein rather than a secreted protein). Suitable proteins from which to derive a transmembrane region include, but are not limited to, coronavirus avian infectious bronchitis virus M protein (IBV-M), cytochrome b6, light harvesting complex protein, early light induced protein of chloroplast, VSV-G, glycophorin, sodium-potassium ATP'ase subunit, glycosyl transferase, mannosidase-2, lamin B receptor, immunoglobulin, with IBV-M protein being particularly preferred.

According to the present invention, an AdM can be linked to a DPM by a DTm. In one embodiment, a DTm comprises the transmembrane region of a DPM. For example, an AdM of the present invention can be linked to an HIV envelope protein containing a transmembrane region capable of inserting into a lipid bilayer. Suitable DPMs that contain a transmembrane region include, but are not limited to, immunoglobulin, viral envelope protein, an enzyme that is involved in lipid production, an enzyme that is involved in steroid production, an enzyme involved in a metabolic pathway, an enzyme whose absence is associated with a disease, an anti-thrombin molecule, an antigen, a toleragen, a cytokine and a toxin.

In another embodiment, a DTm comprises a transmembrane region covalently linked to a DPM, in which the DTm is not derived from the DPM. As used herein, covalent bonds between macromolecular chains refer to bonds that are sufficiently strong to preserve the sequence of subunits of the chain of macromolecules over time. Covalent bonds can include, but are not limited to, disulfide bonds, peptide bonds (e.g., as between two amino acids in a protein sequence), ester bonds, ether bonds, carbon double bonds, carbonyl bonds, phosphodiester linkages and glycosidic linkages. Covalent bonds differ from non-covalent bonds that include ionic bonds, hydrogen bonds and Van Der Waals interactions. A particularly preferred DTm to covalently link to an AdM of the present invention is IBV-M protein.

A preferred DPM of the present invention includes antigens, toleragens, drugs, toxic compounds, markers, hormones, antibodies, cytokines, growth factors, membrane fusion proteins, membrane coat proteins, membrane adhesion proteins, nucleotide binding proteins, venom proteins, electron donor proteins, charge accumulation proteins, assembly proteins, oxidizing proteins, reducing proteins, holding proteins, chaperon proteins, heat shock proteins, cold protectin proteins, osmotic protecting proteins, sweetener proteins, nutritious proteins, enzymes, kinases, cytochromes, electron transport proteins, chelating agents, receptors, signaling molecules, scaffolding proteins, pigment-binding proteins, structural proteins, polymeric proteins, ion-binding proteins, sugar-binding proteins, lipid-binding proteins, metal-binding proteins, calcium-binding proteins, exchange proteins, transport proteins, pore-forming proteins, channel proteins, anchoring proteins, cytoskeletal proteins, junctional proteins, storage proteins, cell wall expanding proteins, contractible proteins, temperature or pH sensitive proteins, mechanotransducing proteins, light-sensitive proteins, light emitting proteins, conductive proteins and regulatory molecules.

In a preferred embodiment, an AgM of the present invention comprises a GUS-IBVM compound. A GUS-IBVM compound of the present invention comprises 0-glucuronidase (GUS; about 73 kD/monomer) covalently linked to an amino acid sequence that comprises amino acids 1 to 225 of the IBV-M integral membrane protein (IBVM; about 25 to 32 kD depending upon the protein's glycosylation profile).

According to the present invention, an AgM can further comprise an anchor domain that is capable of securing (i.e., attaching) an AgM in a lipid bilayer. A suitable anchor domain can anchor itself in a lipid bilayer and thereby prevent the transport of a DTm completely through a lipid bilayer. A preferred anchor domain comprises an amino acid sequence, particularly those that comprises non-polar amino acid residues. A preferred amino acid sequence for use as an anchor domain includes at least a portion of one or more cytoplasmic domains of a transmembrane protein, such as the IBV-M protein.

According to the present invention, an AgM can further comprise a proteolytic restriction site covalently attached or integral with the AgM. As used herein, a proteolytic restriction site refers to an amino acid sequence capable of being cleaved by a protease. Suitable proteolytic restriction sites that are part of or covalently link to an AgM of the present invention include sites that are capable of being cleaved by collagenase, serine proteases, metalloproteases, aspartic acid proteases and/or cysteine proteases, which can be either aminopeptidases, carboxypeptidases or endopeptidases. Preferred proteolytic restriction sites of an AgM include, but are not limited to, sites that are capable of being cleaved by kallikriens, plasminogen activators, thrombin, leucine aminopeptidase, aminopeptidases B and M; astacin-like metalloproteases; calpains; carboxypeptidases A, P and Y; cathepsins, chymotrypsins; cruzipains; meprins; papains; pepsins; renins; thermolysins; trypsins; acrosins, bromelains, elastases, factor Xa, ficins, Staphylococcal V8 proteases, clostopain, and imidodipeptidase.

According to the present invention, a proteolytic restriction site of the present invention can be covalently linked to any portion of an AgM of the present invention. Preferably, a proteolytic restriction site is linked to a portion of a DTm or a portion of a DPM of the present invention, more preferably to a portion of a DTm towards the amino terminal end of the molecule, and even more preferably, an AdM is linked to a DTm by a proteolytic restriction site (e.g., between the carboxy terminus of the AdM and the amino terminus of the DTm). The presence of a proteolytic restriction site in an AgM enables a portion of the AgM to be cleaved from another portion. A portion of an AgM can be cleaved from another portion by contacting the AgM with a protease capable of cleaving the restriction site.

According to the present invention, an AgM can further comprise a leader sequence that is capable of directing the localization of an AgM into a specific membrane compartment of a cell. During protein production in a eukaryotic cell, proteins undergo intracellular transport from their sites of synthesis. One major transport pathway is referred to as the biosynthetic secretory pathway. The biosynthetic pathway involves the exocytosis of proteins from a cell through various routes that employ various organelles. Collectively, the transport system of a cell comprises a continuum of cellular membranes and is referred to herein as an endomembrane system. For purposes of the present invention, an endomembrane system includes the nuclear envelope, ER, ER-Golgi intermediate compartment, Golgi apparatus (e.g., cis and trans-Golgi network), vacuoles and lysosomes, protein bodies, vesicular membranes (e.g., endocytic, secretory, transport and endosomal membrane vesicles) and plasma membrane.

The trafficking of proteins through the various transport routes in a cell is in part regulated by peptide targeting signal sequences, referred to herein as leader sequences. Leader sequences direct proteins to particular cellular organelles. Proteins destined to be secreted from a cell are directed to the ER by a leader sequence referred to as a signal sequence. A signal sequence enables a protein to translocate across the ER membrane, either completely (i.e., into the lumen of the ER) or partially (i.e., remaining bound to the ER membrane by a transmembrane domain). Preferred signal sequences for use with an AgM of the present invention include ER-specific signal sequences. More preferred signal sequences for use with an AgM include IBVM-, VSVG-, SYNVG-, Zein Phytohemagglutinin- and BIP-associated signal sequences.

Further trafficking of proteins in the endomembrane system occurs through the use of retention sequences that retain a protein in a particular membrane compartment. For example, an ER retention sequence prevents a protein from traveling from the ER to the ER-Golgi intermediate membrane or retrieves ER escapees from a Golgi apparatus. Thus, according to the present invention, an AgM can further comprise a retention sequence to target the AgM to a particular membrane compartment. Suitable retention sequences of the present invention include tetrapeptides. Preferred retention sequences include, but are not limited to, outer and inner nuclear envelope-specific sequences, ER-specific sequences, Golgi apparatus-specific sequences, mitochondria-specific sequences, nuclear pore-specific sequences and plastid-specific sequences. Particularly preferred leader sequences include the amino acid sequences Lys-Asp-Glu-Leu (SEQ ID NO:6), His-Asp-Glu-Leu (SEQ ID NO:7), Arg-Gly-Asp-Leu (SEQ ID NO:8), Lys—Lys-X—X (SEQ ID NO:9), Lys-X-Lys-X—X (SEQ ID NO:10), Arg-Lys-Pro-Arg—Arg-E (SEQ ID NO:11) and Arg—Arg-X—X (SEQ ID NO:12), wherein X can be any amino acid residue.

Another aspect of the present invention relates to a nucleic acid molecule that encodes a proteinaceous AgM of the present invention as disclosed herein. According to the present invention, references to nucleic acids also refer to nucleic acid molecules. A nucleic acid molecule can be DNA, RNA, or hybrids or derivatives of either DNA or RNA. Nucleic acid molecules of the present invention can include regulatory regions that control expression of the nucleic acid molecule (e.g., transcription or translation control regions), full-length or partial coding regions, and combinations thereof. Any portion of a nucleic acid molecule of the present invention can be produced by: (1) isolating the molecule from its natural milieu; (2) using recombinant DNA technology (e.g., PCR amplification, cloning); or (3) using chemical synthesis methods. A nucleic acid of the present invention can include functional equivalents of natural nucleic acid molecules encoding an AdM, a DTm, a DPM and/or a anchor domain and may include natural allelic variants and modified nucleic acid molecules in which nucleotides have been inserted, deleted, substituted, and/or inverted in such a manner that such modifications do not substantially interfere with the nucleic acid molecule's ability to encode a protein of the present invention capable of forming oligomers in or in association with a portion of a membrane. Preferred functional equivalents include sequences capable of hybridizing under stringent conditions to at least a portion of or a nucleic acid molecule encoding an AgM (according to conditions described in Sambrook et al., *Molecular Cloning: A Laboratory Manual,* Cold Spring Harbor Labs Press, 1989, which is incorporated herein by reference in its entirety) The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an AgM homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof.

As guidance to what particular modifications can be made at any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a region that is capable of forming an oligomer with another protein, a region capable of inserting into a lipid bilayer and a functional DPM. Functional tests for these various characteristics (e.g., binding studies) allows one of skill in the art to readily modify the protein.

One embodiment of the present invention includes a nucleic acid molecule encoding an AgM having at least two components: (1) an AdM capable of forming oligomers with other AdMs such that the molecules are accumulated in association with or in a portion of a membrane; and (2) a desired product protein functionally associated with said AdM and capable of associating with said lipid bilayer to anchor the AdM to the lipid bilayer. As used herein, "functionally associated" refers to the direct or indirect attachment of a first molecule to a second molecule to form a chimeric compound containing at least the first and second molecules. Suitable and preferred AdMs and DPMs for use in the present invention are heretofore disclosed. A nucleic acid molecule of the present invention comprises at least one nucleic acid sequence encoding an AdM covalently attached (by base pair linkage) to at least one nucleic acid sequence encoding a desired product protein. The nucleic acid sequences are attached in such a manner that the sequences are transcribed in-frame, thereby producing a functional AgM capable of forming oligomers in association with a portion of a membrane.

A portion of each nucleic acid molecule encoding a component (i.e., an AdM or a desired product protein) of an AgM can be covalently associated (using standard recombinant DNA methods) to any other sequence encoding at least a portion of a distinct component to produce an AgM of the present invention. In one embodiment, the 3' end (end encoding the C-terminus) of a nucleic acid molecule encoding an AdM of the present invention is ligated to the 5' end (end encoding the N-terminus) of a nucleic acid molecule encoding a desired product protein.

To obtain membrane-bound embodiments, nucleic acid sequences are used that encode at least one transmembrane domain capable of anchoring an AgM to a membrane. The 3' end of a nucleic acid sequence encoding an AdM is covalently associated (by base pair linkage) to the 5' end of a nucleic acid sequence encoding a transmembrane domain, the 3' end of which is covalently associated with the 51 end of a desired product protein. A nucleic acid molecule encoding an AgM that is capable of being membrane-bound can contain at least one nucleic acid sequence encoding a segment ligated to the 3' end of an AdM in a manner such that the transmembrane encoding sequence is transcribed in-frame.

In other embodiments, a nucleic acid sequence is used that encodes for a signal sequence and/or a retention sequence that is capable of directing the transport of an AgM into a particular organelle of a cell. Nucleic acid sequences encoding the signal sequences are covalently associated (by base pair linkage) to either the 5' end or the 3' end of a nucleic acid molecule. The signal sequence can be a sequence that is naturally associated with an AdM or that is heterologous. Preferred signal sequences are naturally associated sequences. Nucleic acid sequences encoding the retention sequences are covalently associated (by base pair linkage) to either the 5' end or the 3' end of a nucleic acid molecule. The retention sequence can be a sequence that is naturally associated with an AdM or that is heterologous. Preferred retention sequences are heterologous sequences.

Another embodiment of the present invention is a fusion protein that includes an AgM containing-domain attached to a fusion segment. Inclusion of a fusion segment as part of an AgM of the present invention can enhance the molecule's stability during production, storage and/or use. Furthermore, a fusion segment can function as a tool to simplify purification of an AgM, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of the AgM. Linkages between fusion segments and AgMs can be made to be susceptible to cleavage to enable straight-forward recovery of the AgMs. Fusion proteins are preferably produced by culturing a recombinant cell transformed with a fusion nucleic acid sequence that encodes a protein including the fusion segment attached to either the carboxyl and/or amino terminal end of an AgM.

A particularly preferred nucleic acid molecule encoding an AgM includes a nucleic acid sequence encoding a GUS protein ligated to a nucleic acid molecule encoding an IBV-M protein. Particular embodiments of nucleic acid molecules encoding an AgM of the present invention and their construction are described in Example 1.

The present invention also includes a recombinant molecule comprising a nucleic acid sequence encoding an AgM operatively linked to a vector capable of being expressed in a host cell. As used herein, "operatively linked" refers to insertion of a nucleic acid sequence into an expression vector in such a manner that the sequence is capable of being expressed when transformed into a host cell. As used herein, an "expression vector" is an RNA or DNA vector capable of transforming a host cell and effecting expression of an appropriate nucleic acid sequence, preferably replicating within the host cell. An expression vector can be either prokaryotic or eukaryotic, and typically is a virus or a plasmid.

Recombinant molecules of the present invention include pBAP-15, pBI-221, pBI-121, pFG-8, pFG-19, pFG-11A, pFG-14, pFG-13, pFG-20, pFG-22, pFG-21, pFG-23, pFG-5, pDG-71, pDG-714, pDG-715, pFG-2, pDG-716, pFG-3, pDG-712, pFG-1, pFG-15, pFG-18, IBVM/GUS-YEp51, IBVM-PNZ, GUS-pNZ, and GUS-p2UG (described in detail in the Example section).

Construction of desired expression vectors can be performed by methods known to those skilled in the art and expression can be in eukaryotic or prokaryotic systems. Procaryotic systems typically used are bacterial strains including, but not limited to various strains of *E. coli,* various strains of bacilli or various species of Pseudomonas. In prokaryotic systems, plasmids are used that contain replication sites and control sequences derived from a species compatible with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful eukaryotic promoters include early and late promoters from SV40 or other viral promoters such as those derived from baculovirus, polyoma virus, adenovirus, bovine papilloma virus, avian sarcoma virus, tobacco mosaic virus, wound tumor virus, or cauliflower mosaic virus. Expression vectors of the present invention include any vectors that function (i.e., direct gene expression) in recombinant cells of the present invention including bacterial, yeast, other fungal, plant, algal, amoeboid, protozoan, insect, and mammalian cells. Particularly preferred expression vectors of the present invention include CaMV 35S promoter, galactose inducible promoter or glyceraldehyde-3-phosphate dehydrogenase promoter.

An expression system can be constructed from any of the foregoing control elements operatively linked to the nucleic acid sequences of the present invention using methods known to those of skill in the art (see, for example, Sambrook et al., ibid.).

A recombinant molecule of the present invention can be transformed into a host cell to form a recombinant cell. Suitable host cells include bacterial, yeast, other fungal, plant, algal, amoeboid, protozoan, insect, and mammalian cells. A preferred host cell of the present invention includes, but is not limited to, a plant, yeast or animal cell. A more preferred host cell of the present invention includes, but is not limited to, a plant cell, a yeast cell, with a tobacco cell being even more preferred.

It is within the scope of the invention that a host cell can be transformed simultaneously or sequentially with one or more recombinant molecules encoding different AgMs of the present invention. In addition, a host cell can be transformed with additional nucleic acid molecules encoding compounds capable of interacting with or complementing the activity of an AgM of the present invention. For example, a host cell can be transformed with: (1) a recombinant molecule encoding an AgM in which the desired product protein is a subunit of a multimeric protein structure; and (2) a nucleic acid molecule encoding a different subunit of the multimeric protein structure. Also, a host cell can be transformed with: (1) a recombinant molecule encoding an AgM in which the desired product protein is an enzyme; and (2) a recombinant molecule encoding an adjunct molecule capable of regulating the activity of the enzyme. Suitable adjunct molecules include subunits of the enzyme and other members of a metabolic pathway involving the enzyme.

Another aspect of the present invention relates to a method to aggregate a DPM in a portion of a lipid bilayer, comprising aggregating AgMs physically associated with a lipid bilayer by forming oligomers between two or more of the AgMs such that the AgMs are accumulated in association with a portion of the lipid bilayer. In accordance with the foregoing method, the aggregation step of such method can be performed in vitro by contacting AgMs with a lipid-containing substrate either isolated from a cell or synthetically produced. Suitable lipid-containing substrates for use with AgMs include, but are not limited to, artificial or natural lipid-containing substrates, preferably cellular membranes, liposomes and micelles. An AgM of the present invention can be contacted with a lipid-containing substrate using methods standard in the art. For example, multilamellar vesicles can be produced by dissolving lipids in a suitable organic solvent and drying the lipids under vacuum to form a thin lipid film. The film can be covered with an aqueous solution containing AgMs and allowed to hydrate. Another method for preparing lipid vesicles includes the method described in Sprague et al. (*Plant Physiol.* 75:502–504, 1984). In accordance with the foregoing method, a recombinant cell of the present invention can be used to aggregate a DPM in a membrane by culturing such cells under conditions effective to produce such molecules and to allow sequestration of such molecules in or in association with a portion of a membrane in the cell. Effective conditions to produce a recombinant molecule include, but are not limited to, appropriate culture media, temperature, pH and oxygen conditions. Such conditions can vary widely based upon the type of host cell to be transformed with a recombinant molecule of the present invention. Suitable conditions include standard culture conditions known to those of skill in the art for the growth of bacterial, yeast, other fungal, plant, algal, amoeboid, protozoan, insect, and mammalian cells, in particular, yeast and plant cells. Suitable conditions are those that enable a recombinant cell to produce an AgM of the present invention in such a manner that the production does not interfere with the normal functioning of the recombinant cell, such conditions for instance, set forth in the Examples. Other preferred conditions enable a recombinant cell to produce a sufficient number of AgMs such that preferably from about I to about 50 membrane housing compartments and more preferably from about 2 to about 20 membrane housing compartments are formed in the cell (described in detail below). Such membrane housing compartments are substantially similar to the morphology of one or more of the membrane compartments shown in FIG. 4.

A DPM can be sequestered in or in association with a membrane by contacting two or more AgMs with a membrane, and allowing oligomer formation to occur between such aggregate molecules. Traditional methods to produce heterologous proteins in a transgenic host is impeded by such problems as the instability and/or insolubility of the heterologous protein, the loss of activity of the heterologous protein, and the toxicity of the heterologous protein to the host. Applicants have discovered that the expression of recombinant molecules encoding AgMs of the present invention overcome such problems by sequestering heterologous proteins away from the remainder of the cellular contents soon after biosynthesis of such proteins. Thus, an advantage of using the cellular aggregation method of the present invention is that the sequestration of the Agm in or in association with a portion of a membrane limits exposure of such protein to degradation by proteases and preserves the activity of the protein. Another advantage of such method is that the sequestration avoids the aggregation of the heterologous protein into insoluble particles which renders the protein essentially useless. Such sequestration prevents the interference of normal cellular function that would otherwise result from the presence of high concentrations of heterologous protein.

Novel protective qualities of the cellular aggregation method of the present invention are achieved by targeting AgMs so that they accumulate in or in association with cellular membranes. Applicants have discovered that AgMs that accumulate in a portion of the endomembrane system are protected due to the generation of stacked and/or planar membrane structures created by the aggregation of such molecules. Previous investigators have reported stacked membrane structures referred to as karmellae (Wright et al., *J. Cell. Biol.,* 107:101–114, 1988; Wright et al., *The New Biologist,* 2:915–921, 1990; Wright et al., *Methods in Cell Biol.,* 31:473–512, 1989; and Koning et al., *Cell Motil. Cytoskel.,* 25:111–128, 1993). Such karmellae, however, differ from the stacked membranes of the present invention in that the karmellae occur naturally through non-specific interactions between proteins and lipids, and are not the result of association by and between AgMs. In addition, naturally-occurring karmellae have only been observed in yeast. The stacked membranes of the present invention can be produced in non-yeast cells, such as plant cells.

According to the present invention, a recombinant cell line expressing an AgM of the present invention can preferably survive for at least about 6 months, more preferably at least about 12 months and even more preferably at least about 24 months.

In a preferred embodiment, a non-naturally occurring membrane housing compartment is produced by the method comprising: (1) transforming a tobacco cell with a recombinant molecule encoding GUS protein and IBV-M protein to form a recombinant cell; (2) culturing the recombinant cell to produce a GUS-IBV-M chimeric protein and to allow the chimeric protein accumulate in a portion of an ER membrane.

A non-naturally occurring membrane housing compartment can be formed using eukaryotic or prokaryotic membranes. Preferred membranes include, but are not limited to, a fungal membrane, a protozoan membrane, an algal membrane, an amoeboid membrane, a bacterial membrane, a yeast membrane, an animal membrane and a plant membrane. These preferred groups of membranes include outer cell membranes, inner cell membranes and organelle membranes. Suitable organelle membranes for use with the present invention include, but are not limited to, a plasma membrane, an endocytic vesicle membrane, a lysosomal vesicle membrane, a secretory vesicle membrane, a transport vesicle membrane, an endosomal membrane system, a mitochondria membrane, an endoplasmic reticulum membrane, nuclear envelope membrane, a Golgi apparatus membrane, a trans-Golgi network membrane, a cis-Golgi network membrane, a yeast cell vacuole membrane, a plastid, a peroxisome membrane, and different collections thereof. Particularly preferred membranes useful for association with an AgM include an endoplasmic reticulum and a nuclear envelope membrane.

A non-naturally occurring membrane housing compartment is formed by the method comprising aggregating AdMs physically associated with a lipid bilayer in such a manner that the molecules are associated with a portion of the lipid bilayer. A stacked membrane housing compartment is formed when the AdMs are located on the cytoplasmic side of the lipid bilayer. A stacked membrane can also be referred to as a zippered-membrane (Z-membrane). Thus, an AgM useful for forming stacked membrane housing compartments comprises a signal sequence attached to the amino terminal end of an AdM, which is attached to a DPM by a transmembrane domain. A planar membrane housing compartment is formed when the AdMs are located on the lumenal side of a lipid bilayer. Thus, an AgM useful for forming planar membrane housing compartments comprises a signal sequence attached to the amino terminal end of a DPM, which is attached to an AdM by a transmembrane domain. Preferably, a non-naturally occurring membrane housing compartment is formed by forming oligomers between a sufficient number of AdMs such that a membrane compartment is formed that is substantially similar to the morphology of one or more of the membrane compartments shown in FIG. 4.

In conjunction with the aforementioned cellular aggregation method, the present invention includes a non-naturally occurring membrane housing compartment comprising an intracellular structure that sequesters proteins inside of a cell in such a manner that the sequestration does not substantially interfere with cellular function. A non-naturally occurring membrane housing compartment can be characterized by its size and morphology, as well as by the membrane in which it is produced. Preferably, a concentric non-naturally occurring membrane housing compartment is from about 0.5 $\mu$m to about 4.0 $\mu$m in diameter, more preferably from about 1.0 $\mu$m to about 3.5 $\mu$m, and even more preferably from about 1.5 $\mu$m to about 3.0 $\mu$m in diameter when visualized using transmission electron microscopy. Preferably, a non-naturally occurring membrane housing compartment that is not concentric has from about 2 to about 10 stacked membranes, more preferably from about 3 to about 8 membranes and even more preferably from about 5 to about 6 membranes.

The general morphology of a non-naturally occurring membrane housing compartment of the present invention stacked and/or planar membrane structures. A stacked membrane structure comprises the juxtaposition of one lipid bilayer on top of or below another lipid bilayer when the bilayers are viewed in cross-section. A planar membrane structure comprises two-bilayer membranes whose lumenal surfaces are pulled together by an AgM. A preferred non-naturally occurring membrane housing compartment of the present invention has a morphology substantially similar to the morphology of one or more membrane compartments shown in FIG. 4.

One embodiment of the present invention comprises a method for increasing the concentration of a desired product molecule within a cell, the method comprising forming within a cell oligomers between two or more aggregate molecules having desired product molecules attached thereto, wherein the concentration of the desired product molecules in the cell exceeds the concentration of the desired product molecules in cells where said oligomers are not formed. Preferably, the concentration of the desired product molecule in the cell in which oligomers have formed is about 10%, more preferably about 5% and even more preferably about 2% of the total protein of a cell. Also preferably, the concentration of the desired product molecule in the cell in which oligomers have formed is about 30%, more preferably about 20% and even more preferably about 10% of the protein in the membrane fraction of a cell.

The novel protective qualities of a membrane housing compartment formed by AgMs of the present invention provides for numerous uses. For example, an AgM of the present invention can be used to increase the concentration of a DPM inside a cell without affecting the normal function of that cell. Thus, cells can be used to produce amounts of a DPM that were heretofore unattainable using conventional techniques without sequestration within the cell. Without sequestration, high concentrations of DPMs can reach toxic levels in which the DPMs inhibit the normal functioning of the cell.

Another aspect of the present invention relates to the use of recombinant cells to produce at least one AgM by culturing such cells under conditions effective to produce such molecules, and recovering such molecules. Effective culture conditions to produce an AgM can be determined by one of skill in the art based upon the cell type of the recombinant cell. Depending on the expression vector used for production, resultant AgMs can either remain within the recombinant cell, or be secreted into the culture medium. As used herein, the term “recovering the molecule” refers to collecting the fermentation medium containing the molecule and/or recombinant cells. Recovery need not imply additional steps of separation or purification. AgMs of the present invention can be purified using a variety of standard purification techniques such as, but not limited to affinity chromatography, ion exchange chromatography, filtration, centrifugation, electrophoresis, hydrophobic interaction chromatography, gel filtration chromatography, chromatofocusing and differential solubilization. Soluble AgMs of the present invention can be purified using, for example, immunoaffinity chromatography. AgMs anchored in a lipid bilayer can be recovered by, for example, density gradient centrifugation of purified membranes treated with Triton X-100 or other detergents.

Isolated AgMs are preferably retrieved in “substantially pure” form. As used herein, “substantially pure” refers to a purity that allows for the effective use of the molecule as a heretofore described pharmaceutical composition, diagnostic reagent or experimental reagent.

A DPM can be separated from an AgM using protease digestion. In particular, a DPM can be cleaved from an AgM using a protease capable of cleaving an amino acid sequence at a desired proteolytic restriction site contained in the AgM.

A further aspect of the present invention includes a delivery vehicle capable of delivering an AgM to a cell or an organism. In particular, cells having desired concentrations of a particular DPM sequestered therein can be fed to an animal to achieve delivery of such DPM. A delivery vehicle of the present invention comprises a recombinant cell expressing at least one nucleic acid molecule encoding an AgM. Suitable product molecules to be delivered include, but are not limited antigens, toleragens, drugs (e.g., antibiotics or aneoplastic drugs), toxic compounds, markers, hormones, antibodies, cytokines, growth factors. More preferred product molecules to be delivered include a protein, a peptide, an oligosaccharide, a polysaccharide, a toxin, and a dye. It is within the scope of the invention that a recombinant cell useful as a delivery vehicle can be have two or more nucleic acid molecules encoding two or more different product molecules.

A host cell suitable for producing a recombinant cell useful as a delivery vehicle includes, but is not limited to, a cell capable of being consumed by an animal, a cell that is capable of fusing with another cell and a cell that can be invaded by an infectious agent. Preferably, a cell that is capable of being consumed by an animal includes, for example, insect, plant, bacterial, algal, yeast or other fungal, amoeboid, animal, protozoan cells and mixtures thereof, more preferably a plant cell, bacteria cell, yeast or other fungal cell, and mixtures thereof, and even more preferably a plant cell. If a plant cell is used as a delivery vehicle, the expression of nucleic acid molecules transformed into such cells can be under the control of a tissue specific promoter. For example, promoters can be used that allow specific expression of a nucleic acid molecule in the stem, leaf or root of a plant. Such tissue specific expression enables one to feed a portion of a plant to an animal based on the animals digestive system and preferred diet.

Due to the protective qualities of a membrane housing compartment, AgMs of the present invention can be used to aggregate and store DPMs in membrane housing compartments. As such, another aspect of the present invention includes a command secretion system comprising a recombinant cell in which membrane-bound DPMs are secreted from the cell upon exposure of the cell to a secretion inducing agent. A command secretion system of the present invention comprises: (1) a recombinant cell comprising; (a) a nucleic acid molecule encoding an AgM comprising an AdM and a DPM, in which the DPM is linked to the AdM by a DTm, the DPM being covalently attached to a proteolytic restriction site, and (b) a nucleic acid molecule encoding a protease that is capable of cleaving the DPM from the DTm at a proteolytic restriction site; and (2) an inducing agent capable of inducing the expression of the nucleic acid molecule encoding the protease. Particularly preferred nucleic acid molecules for use in the command secretion system of the present invention encode signal sequences.

Suitable and preferred proteolytic restriction sites and proteases for use in a command secretion system are heretofore disclosed. In a preferred embodiment, a nucleic acid molecule encoding a protease is operatively linked to an inducible promoter. A variety of such inducible promoter sequences are known to those skilled in the art. Suitable inducible promoters include promoters in which the promoter directly regulates the expression of a gene, or promoters that regulate the expression of genes that encode proteins involved in repressible and otherwise inducible systems. Preferred inducible promoter sequences include those which function in mammalian, plant, yeast or other fungal, bacterial, algal, protozoan, and amoeboid cells. More preferred inducible promoters include, but are not limited to, tac, lac, trp, trc, oxy-pro, bacteriophage lambda ($\lambda$) (such as $\lambda p_L$ and $\lambda p_R$) T7lac, metallothionein, Pichia alcohol oxidase and the yeast ADH2/GAPDH promoter. In accordance with the foregoing system, the choice of inducing agent to be used in the system is dependent upon the type of inducible promoter operatively linked to the nucleic acid molecule encoding the protease. An effective amount of inducing agent to administer to a recombinant cell is based upon, for example, the type of agent and promoter (e.g., tissue specific promoters in plants, or yeast promoters) used and the type of recombinant cell used. Determination of the type and the amounts of a protease can be accomplished by those skilled in the art depending upon such variables.

The protective qualities of a housing compartment of the present invention enables one to accumulate rare intracellular molecules (i.e., molecules present in low concentrations in a cell) by binding such rare molecules to DPMs that are aggregating or aggregated in a membrane housing compartment of the present invention. The aggregation step effectively concentrates the rare molecules in the housing compartment, which can then be isolated.

Thus, the present invention also includes an assay for identifying protein associated molecules, comprising: (1) contacting a first AdM of the present invention functionally attached to a first subunit of a protein formation with a second AdM of the present invention functionally attached to a second subunit of the protein formation to form a sequestered protein complex; (2) contacting the sequestered protein complex with a putative associated molecule; and (3) determining if the putative associated molecule is capable of associating with the sequestered protein complex by assessing the binding of the putative associated molecule to the sequestered protein complex. According to the present invention, an associated protein molecule can comprise any molecule capable of specifically associating with a protein. For example, a cellular receptor complex can comprise a receptor having multiple receptor subunits that regulate the ability of the receptor to stimulate cytoplasmic signal transduction molecules. Also, a DNA binding protein complex can comprise a DNA binding protein having multiple DNA binding protein subunits that regulate the ability of the complex to transcribe DNA. Such receptor and DNA binding protein subunits are examples of associated protein molecules. According to the present invention, the first and second subunits of the protein formation can be identical or different.

In one embodiment, a recombinant cell of the present invention is used to identify protein associated molecules. In accordance with the foregoing assay, recombinant molecules encoding a first AdM and a second AdM are expressed in a recombinant cell suspected of expressing one or more molecules capable of associating with the first and/or second subunits functionally attached to the AdMs. A putative associated molecule can be identified by culturing cells under conditions effective to promote the formation of sequestered protein complexes, and recovering such complexes. Effective culture conditions to produce such complexes can be determined by one of skill in the art based upon the cell type of the recombinant cell. For example, a plant cell can be cultured in an effective culture medium at 25° C. for 24 hours to produce a protein complex. The presence of a protein associated molecule can be determined by characterizing the components of the sequestered protein complexes using standard protein chemistry and immunochemistry techniques known in the art. Such an in vivo assay has the advantage of enabling detection of protein associated molecules that may be present in small amounts.

Another embodiment relates to an in vitro assay for identifying protein associated molecules. First and second AdMs are contacted in the presence of an isolated lipid-containing substrate to form sequestered protein complexes in or in association with the substrate. The sequestered protein complexes are then contacted with a homologous or heterologous population of putative associated molecules under conditions suitable for binding between such complexes and molecules. Suitable conditions for binding can be determined by one of skill in the art based upon, for example, the characteristics of the subunit functionally attached to the AdM, the purity of the putative associated molecule population and the predicted binding affinity of a putative associated molecule contained in the population.

The assay of the present invention is particularly useful for identifying a putative associated molecule that includes, but is not limited to, a subunit of a multi-subunit protein complex, a cofactor, a signal transduction protein, a cytoskeletal protein, an organelle associated protein, a secretory pathway associated protein, an excretory pathway associated protein, or an extracellular matrix protein. Methods to detect the association of a putative associated molecule to a sequestered protein complex are known to those of skill in the art and include, for example, affinity chromatography, ion exchange chromatography, electrophoresis, hydrophobic interaction chromatography, gel filtration chromatography, chromatofocusing, centrifugation, electron microscopy and high pressure liquid chromatography.

Another aspect of the present invention includes a biological sensor system comprising AgMs physically associated with a lipid bilayer in such a manner that the AgMs are accumulated in association with a portion of a lipid bilayer, the AgMs being functionally associated with a biological sensing molecule. Preferred biological sensing molecules include, but are not limited to, molecules that are capable of responding to light, chemicals, temperature, pH, ions, heavy metals, gases or electric fields. More preferred biological sensing molecules include, but are not limited to, light, chemicals and heavy metals. A biological sensing system of the present invention can be produced in vivo or in vitro using the aggregation methods heretofore described.

Another aspect of the present invention includes a metabolic pathway system comprising AgMs physically associated with a lipid bilayer in such a manner that the AgMs are accumulated in association with a portion of a lipid bilayer, the AgMs being functionally associated with different enzymes involved in a metabolic pathway. For example, AgMs can be used to construct a lipid modification pathway by aggregating an AgM functionally associated with a fatty acid elongase to another AgM functionally associated with a desaturase, and so on. A metabolic pathway system of the present invention can be produced in vivo or in vitro using the aggregation methods heretofore described.

In one embodiment, the present invention includes a method to detoxify a cell, comprising: (1) providing to a cell an adhesive molecule having at least one site capable of binding to a free-floating toxin; and (2) contacting the adhesive molecule with a toxin, whereby the adhesive molecule and toxin form an aggregate, wherein the aggregate is less toxic to the cell than the free-floating toxin. A free-floating toxin refers to a toxin that is not associated with an adhesive molecule of the present invention. A preferred toxin to bind to an adhesive molecule includes heavy metal binding proteins, viral proteins and nucleic acids.

In another embodiment, the present invention includes a method to detoxify a cell, comprising: (1) providing an aggregate molecule comprising an adhesive molecule covalently attached to a detoxifying enzyme; and (2) contacting the aggregate molecule with a free-floating toxin, wherein the aggregate molecule inactivates the toxin. A preferred detoxifying enzyme to attach to an AdM of the present invention includes cytochrome P450.

In another embodiment, the present invention includes a method to degrade cells for fuel production. According to this method, plant material can be degraded to recover fuel, such as ethanol. According to the present method, plans comprising an AgM covalently attached to a plant cell wall degrading enzyme can be harvested and stored. Through natural senescence, proteases stored in the vacuoles of the plant cells will release proteases capable of cleaving the proteolytic site contained in the AgM, thereby releasing the cell wall degrading enzyme for the AgM. The cell wall degrading enzyme is then free to degrade the plant cell wall. The method to degrade cells for fuel production includes: (1) providing an aggregate molecule comprising an adhesive molecule having a proteolytic restriction site covalently attached to a plant cell wall degrading enzyme; and (2) contacting the aggregate molecule with a protease, wherein the cell wall degrading enzyme is cleaved from the aggregate molecule by the protease. Preferably, plants for use with the present method include cereal or fiber plants and more preferably corn plants. Suitable proteolytic restriction sites for use in the present fuel production method include those proteolytic restriction sites disclosed in detail herein. Preferred proteolytic restriction sites include sites susceptible to cleavage by corn plant proteases.

The following experimental results are provided for purposes of illustration and are not intended to limit the scope of the invention.

EXAMPLES

Example 1

This example describes the production of gene constructs encoding GUS protein or VSVG protein associated with IBVM or VSVG transmembrane domains.

A series of expression vectors were constructed and are summarized in Table 1. The method of construction is described in detail below.

TABLE 1

Summary of the DNA plasmids employed for protoplast transformation and leaf-disc transformation of tobacco

| Gene Constructions | Transient Expression Cassettes | Binary Vectors for Transformation |
|---|---|---|
| CaM V 35S-35S~GUS~CaM V Poly A$^+$ | pBAP-15 | not available |
| CaM V 35S~GUS~nos terminator | pBI-221 | pBI-121 |
| CaM V 35S-35S~M~CaM V Poly A$^+$ | pFG-8 | pFG-19 |
| CaM V 35S-35S~IBVM-GUS~CaM V Poly A$^+$ | pFG-11A | pFG-14 |
| hsp6871~IBVM-GUS~CaM V Poly A$^+$ | not available | pFG-13 |
| CaM V 35S-35S~IBV-m1-Δ-GUS~ CaM V Poly A$^+$ | pFG-20 | pFG-22 |
| CaM V 35S-35S~Gm-1~CaM V Poly A$^+$ | pFG-21 | pFG-23 |
| CaM V 35S-35S~VSVG~CaM V Poly A$^+$ | pFG-5 | not available |
| CaM V 35S~VSVG~nos terminator | pDG-71 | pDG-714 |
| CaM V 35S~VSVG-TA1~nos terminator | pDG-715 | pFG-2 |
| CaM V 35S~VSVG-TA2~nos terminator | pDG-716 | pFG-3 |
| CaM V 35S~VSVG-TA1,2~nos terminator | pDG-712 | pFG-1 |

A. Construction of the Expression Vector Containing CaM V 35S—35S~M~CaM V Poly A$^+$ The expression vector for cloning IBVM DNA was constructed by excising the DNA sequence encoding the full length M protein from pSV/-E1 (Machamer et al., 1987) using the restriction enzyme Xho I. The IBVM DNA was ligated into the Sal I site of the Sal I digested vector pJIT-117 (Guerineau et al., 1988) by blunt end ligation. The resultant plasmid pFG-8 containing the IBVM DNA provides regulated transcription of inserted coding sequence by a double Cauliflower Mosaic Virus 35S promoter (CaMV 35S—35S), and by the corresponding 3' non-translated polyadenylation signal (Poly $A^+$ terminator) of the same gene. The plasmid also contains an origin of replication site and a β-lactamase gene that confers ampicillin resistance.

B. Construction of an Expression Vector Containing CaM V 35S—35S~IBVM-GUS~CaM V Poly $A^+$ Using pSV/-E1 as a template (Machamer, ibid.), two synthetic primers (5'-primer: 5'-GCG CGT CGA CCG ACC ATG TCC AAG GAG ACA AAT-3' SEQ ID NO:1, 3'-primer: 5'-GGC CCC CAT GGT GTA AAG ACT ACT TCC-3' SEQ ID NO:2) were used to isolate IBVM DNA encoding the full length protein by polymerase chain reaction (PCR). The 5'-primer encodes a unique Sal I site upstream of the translation start site. The 3'-primer has the effect of eliminating the stop codon from the open reading frame of the IBVM protein and encodes a unique Nco I site.

The DNA encoding full length GUS protein was then isolated by digesting the plasmid pRAJ-275 (Clontech, Calif., USA) with Hind III and EcoR I to obtain a 1.8 kb GUS-containing fragment. The 1.8 kb fragment was ligated into the larger segment of Hind III/EcoR I digested pJIT-117 plasmid (Guerineau et al., ibid.) that had been treated with gene-clean. The resultant plasmid, pBAP-15, has unique Hind III, Sal I and Nco I sites between the CaMV 35S—35S promoter, GUS DNA and a poly $A^+$ terminator sequence downstream from the GUS coding sequence.

A polylinker containing Hind III, Sal I and Xho I sites in sequential order was isolated by digesting pBluScript SK(-) (Stratagene, La Jolla, Calif.) with Hind III and Xho I and obtaining a 25 bp fragment. pBAP-15 plasmid was then digested with Hind III and Sal I, treated with CIAP (Calf Intestinal Alkaline Phosphatase; Promega, Madison, Wis.) and ligated with the polylinker 25 bp fragment to create an intermediate plasmid referred to as pFG-10. This method of construction resulted in the separation of the Sal I and Nco I sites in pBAP-15, thereby enabling these sites to be used simultaneously for cloning purposes.

The IBVM coding sequence that was produced by PCR was digested with Sal I and Nco I, and ligated into pFG-10 plasmid that had been digested with Sal I and Nco I and treated with CIAP. The resultant construct, pFG-11A, contains IBVM DNA and GUS DNA having a perfectly aligned translation junction. The transcription is under the regulation of a CaMV 35S—35S promoter and a Poly $A^+$ terminator site. The plasmid also contains an origin of replication site and a β-lactamase gene that confers ampicillin resistance.

C. Construction of an Expression Vector Containing CaM V 35S—35S~-ml-Δ-GUS~CaM V Poly $A^+$ An expression vector was prepared encoding full length GUS protein and a modified M protein lacking two of three M transmembrane domains, referred to as IBV-m1Δ-GUS. The expression vector encoding IBV-m1Δ-GUS was constructed using the techniques described above for the production of pFG-11A (see section B) except a different 3'-primer (5'-GGC CCC CAT GGT ATA AAT AAC CTT ACT TCT-3' SEQ ID NO:3) was used for the PCR amplification. This primer amplifies the DNA sequence encoding the first 49 N-terminal amino acids of M, the first transmembrane domain (i.e., ml) and the partial cytoplasmic loop located between the ml and the second transmembrane domain (m2). The resultant plasmid is referred to as pFG-20.

D. Construction of an Expression Vector Containing hsp6871~IBVM-GUS-CaM V Poly $A^+$ An expression vector was prepared encoding full length GUS and M protein under the control of the hsp6871 promoter. For the conditional expression of the DNA encoding the IBVM-GUS protein, the CaMV 35S—35S promoter of pFG-11A was replaced with a soybean hsp6871 promoter (Baumann et al., 1987), then the complete expression vector was ligated into pBIN-19. The resultant plasmid is referred to as pFG-13.

E. Construction of an Expression Vector Containing CaM V 35S—35S~Gm 1~CaM V Poly $A^+$ An expression vector was prepared that encodes a chimeric protein comprising VSVG protein in which the VSVG transmembrane domain has been replaced by the m1 transmembrane domain from M protein. The chimeric protein is referred to as Gm-1. The DNA encoding Gm-1 was isolated from the plasmid pT7/Gm1 (Swift et al., 1991) by digesting the plasmid with Xho I to produce a 1.67 kb fragment. The Gm1-containing fragment was ligated into pJIT-117 (Guerineau et al., ibid.) that had been digested with Sal I. Following ligation, clones having the Gm1 encoding sequences in the correct orientation were identified by restriction digest analysis. The resultant plasmid is referred to as pFG-21.

F. Construction of Expression Vectors Containing CaM V 35S—35S~VSVG~CaM V Poly $A^+$ and Mutants The expression vectors encoding wild type VSVG protein (referred to as pFG-5) and mutant VSVG protein (referred to as pDG-71, pDG-712, pDG-715 and pDG-716) were constructed as described (Galbraith et al. 1992). The plasmid pFG-5 contains a nucleic acid sequence encoding wild type VSVG, a CaMV 35S—35S promoter and Poly $A^+$ terminator. The plasmid pDG-71 contains a nucleic acid sequence encoding wild type VSVG, a CaMV 35S—35S promoter and the nopaline-synthetase (nos) terminator. The plasmid pDG-715 contains a nucleic acid sequence encoding a mutant VSVG lacking the first glycosylation site of VSVG, a CaMV 35S—35S promoter and the nos terminator. The plasmid pDG-716 contains a nucleic acid sequence encoding a mutant VSVG lacking the second glycosylation site of VSVG, a CaMV 35S—35S promoter and the nos terminator. The plasmid pDG-712 contains a nucleic acid sequence encoding a mutant VSVG lacking the both N-linked glycosylation sites of VSVG, a CaMV 35S—35S promoter and the nos terminator.

G. Construction of an Expression Vector Containing CaM V 35S~SYNVG~nos terminator An expression vector encoding SYNVG protein was prepared as follows. A nucleic acid molecule encoding SYNVG protein lacking a leader sequence was produced by PCR amplification of a 1.97 kb fragment using the plasmid pGT-573 (Goldberg et al., 1991) as template and two primers (5'-primer: 5'-CCC TCG AGA TGT CTC ATA TAA TGA ACC TT-3' SEQ ID NO:4 and 3'-primer: 5'-GGG GTA CCT TCA GAT GTC GTT CAG AA-3' SEQ ID NO:5). The amplified fragment contains an Xho I site prior to the initiation codon and a Kpn I site after the stop codon. The fragment was then digested with Xho I and Kpn I, and ligated into the 3.75 kb segment of the pDG-711 which had been digested with Xho I and Kpn I. The resultant plasmid is referred to as pFG-15. The plasmid contains a single CaMV 35S promoter and a nos terminator.

Example 2

This example describes the transformation and analysis of protoplasts treated with the expression vectors of Example 1.

A. Protoplast Isolation

Protoplasts were prepared from leaf tissues of axenic cultured tobacco plantlets as follows.

Well expanded axenic plantlets of tobacco suitable for protoplast isolation were generated and maintained essentially according to the method described in Murashige et al. (*Physiol. Plant* 15:453–497, 1962) with slight modifications according to Harkins et al. (*Proc. Natl. Acad. Sci.* 87:816–820, 1990). Protoplasts were isolated from well expanded axenic plantlets of tobacco essentially according to the method described by Harkins et al. (ibid.).

B. Transformation of Tobacco Protoplasts

Tobacco protoplasts were transfected with the expression vectors pFG-5, pFG-8, pFG-11A, pFG-15, pFG-20, pFG-21, pBAP-15, pFG-71, pDG-712, pDG-715, or pDG-716 using essentially the same method described by Harkins et al. (ibid.), which is a modified version of the procedure described by Negrutiu et al. (*Plant Mol. Biol.* 8:363–373, 1987).

Example 3

This example describes Western blot analysis of tobacco leaf protoplasts transformed with plasmids encoding VSVG and SYNVG protein.

Samples derived from tobacco leaf protoplasts transformed with pFG-21 (Gm-1), pDG-71 (VSVG) pFG-5 (VSVG) and pFG-15 (SYNVG) plasmids produced in Example 2 were analyzed by Western blot to detect expression of such proteins in the protoplasts.

A. VSVG Protein Expression

About $15 \times 10^4$ to about $3.0 \times 10^5$ viable protoplasts transformed with pFG-21 (Gm-1), pDG-71 (VSVG) and pFG-5 (VSVG), about 18–24 hours after incubation in darkness, were purified by sucrose floatation as described in Example 2. The protoplasts were pelleted and resuspended in 2× SDS-sample buffer. In addition, protein was prepared from untransformed protoplasts as a negative control sample.

Equivalent volumes of sample were loaded onto a one-dimensional sodium dodecyl sulfate-polyacrylamide gel electrophoresis (SDS-PAGE; Laemmli, *Nature* 227:680–685, 1970) having a 4% stacking gel and a 7.5% running gel. The running gels are buffered with 0.375 M Tris (pH 8.8) and 0.1% SDS. For gels containing more than 10% of the monomer mixture, glycerol is added to a final concentration of 5% (v/v), in order to prevent gel cracking. The stacking gets comprise 4% of the monomer mixture, and are buffered with 0.125 M Tris (pH 6.8) and 0.1% SDS. The stacking and running gel solutions are degassed using a vacuum, then polymerized with ammonium persulfate (0.75 µg/mL gel solution) and TEMED (0.75–1.0 µL/mL gel solution).

For each lane of gel, the protein was adjusted with 2× SDS-sample buffer to give final 1× concentration of buffer in the samples, which thus contain 0.0625 M Tris (pH 6.8), 2% SDS, 10% glycerol, 5% β-mercaptoethanol, and a trace amount of Bromophenol blue dye. The sample mixtures were boiled in water bath for 5 minutes, and centrifuged in a microfuge for 3–5 minutes. The supernatant was loaded onto a gel. Gels were generally run at 100 Volts for 1 to 1.5 hours or until the dye front reaches the bottom of the running gel.

After completion of gel electrophoresis, the gels were soaked in cold Matsudaira transfer buffer (10% methanol, 10 mM CAPS pH 10.5) for 5 minutes. The soaked gels were blotted onto polyvinylidene difluoride membrane (Immobilon; Millipore Corp., Bedford, Mass.). Proteins were electrically transferred from gels to the membranes in cold Matsudaira transfer buffer under constant voltage (100 Volts) and cold circulation for 1 hour. The blotted membranes were washed in deionized water prior to incubation with an appropriate antibody.

The blotted membranes were washed 2 times (first for 60 minutes, then for 30 minutes) with gentle shaking in TSW medium (10 mM Tris [pH 7.4], 0.9% NaCl, 0.25% gelatin, 0.1% Triton X-100 and 0.02% SDS) and then incubated in TSW medium plus primary antibodies for 1 hour at room temperature. The membranes were then washed twice (15 minutes each) in TSW medium. The membranes were then incubated in TSW medium plus secondary antibodies. The membranes were then washed twice (15 minutes for each) in TSW medium and one time (about 5 minutes) in color development solution (100 mM Tris, 100 mM NaCl, 5 mM $MgCl_2$, pH 9.5). Final color development was conducted in the color development solution plus 33 µg/mL 5-bromo-4-chloro-3-indolyl phosphate and 66 µg/mL nitroblue tetrazolium for 30 minutes or until protein bands appear on blots. The developed blots were then washed with water.

The following antibodies were used. Expression of Gm-1 protein was detected by incubating a blot with using polyclonal rabbit anti-VSV serum at a 1:2,500 dilution (provided by Dr. Machamer, Johns Hopkins University, Baltimore, Md.) and secondary antibody, goat anti-rabbit IgG (H+L) alkaline phosphatase conjugate, at a dilution of 1:10,000 (Sigma, St. Louis, Mo.). VSVG protein was detected by incubating a blot with using polyclonal rabbit anti-VSV serum at a 1:1,600 dilution (provided by Dr. H.-P. H. Moore, University of California at San Francisco, San Francisco, Calif.) and secondary antibody, goat anti-rabbit Ig G (H+L) at a dilution of 1:2,000 (Bio-Rad, Hercules, Calif.).

Immunoblotting results indicated that expression of both the pFG-21, pDG-71 and pFG-5 plasmids in tobacco leaf protoplasts resulted in the expression of two immunoreactive proteins. A first protein having a molecular weigh of about 61 kD and a second protein having a molecular weight of about 52 kD. The results indicate the existence of two isoforms of VSVG protein in the protoplasts.

Promoter strength was assessed by densitometric analysis of intensity between immunoreactive proteins encoded by pDG-71 (single CaM V S35 promoter) and pFG-5 (double CaM V S35 promoter). The blots were digitized into TIF formatted files using a 256 grayscale either with a Stratascan™ 7000 Scanning System (Stratagene, La Jolla, Calif.) or a Star I Digital CCD Camera System (Photometrics, Phoenix, Ariz.), and analyzed with Stratascan™ 2D Densitometry Software from Stratagene. The combined intensity of the larger and the smaller isoforms regulated by the CaM V double 35S promoter (pFG-5) was found to be about three times that by the CaM V single 35S promoter (pDG-71). Comparisons of the two isoforms within each treatment indicated that the larger isoform of VSVG was predominant for the single promoter, whereas the larger and the smaller isoforms were roughly equal under the double promoter, when the incubation of the transfected protoplasts only lasted 18 hours. This indicates that the biosynthesis and the conversion of the larger isoform is quicker under the double 35S promoter.

Example 4

This example describes the analysis of β-Glucuronidase activity in samples derived from protoplasts transformed with IBVM-GUS encoding plasmid.

About 10,000 viable protoplasts either transformed with pBAP-15 (wild type GUS), pFG-11 (IBVM-GUS chimera), pFG-20 (IBV-m1Δ-GUS) or transformed without expression vector were purified sucrose floatation about 20–24 hours after transformation, according to the method described in Example 2. The protoplasts were lysed in 1× extraction buffer to test for β-Glucuronidase (GUS) activity according to the method disclosed in Jefferson et al. (*EMBO J.* 6:3901–3907, 1987). Specific GUS activities of the samples (arbitrary fluorescence units) were determined in a 96-well plate using a Fluoroskan II fluorometer (excitation at 365 nm, emission at 455 nm). Five time points (0, 15, 30, 45, 60 minutes), each with 2 replications, were sampled for kinetics analysis. Total GUS activities were normalized based on equal amounts of total proteins in each treatment.

GUS activity of the IBVM-GUS chimeric proteins (pFG-11) was easily detected through enzymatic analysis of transfected protoplasts when compared with protoplasts transformed with wild type GUS encoding plasmid (pBAP-15) or with no plasmid DNA (negative control). The baseline GUS activity values were derived from the negative control sample and were found to be between about 5 to about 20 fluorescence unit per minute (Fu/min). GUS activities in protoplasts transformed with pFG-11 were about 160 Fu/min. GUS activities in protoplasts transformed with pBAP-15.

Protoplasts transformed with pFG-20 (-m1Δ-GUS) showed similar patterns of GUS activity as the pFG-11 results. Protoplasts transformed with pFG-20 had GUS activities of from about 2000 to about 2200 Fu/min, while the negative control had a Fu/min value of about 0. Protoplasts transformed with pBAP-15 had GUS activities of from about 13800 to about 14000 Fu/min.

The results using both pFG-11 and pFG-20 IBVM-GUS encoding plasmids indicate that these plasmids encode functional GUS protein in tobacco leaf protoplasts.

Example 5

This example describes the transformation of Tobacco plants with various expression vectors described in Example 1.

A. Transformation of Tobacco Plants

Plant transformation is carried out as described by Horsch et al. (*Proc. Natl. Acad. Sci.* 83:4428–4436, 1986). To transform the DNA encoded by the expression vectors described in Example 1 into *N. tabacum* cv. Xanthi, the following procedure was used. The plasmids pFG-8, pFG-11A, pFG-15, pFG-File 20, pFG-21, pDG-712, pDG-715 and pDG-716 were digested with either Pvu II, Kpn I, Hind III+EcoR I or Sst I+Xho I to isolate the appropriate regulatory and coding sequences for ligation into the corresponding enzyme-cut, CIAP-treated pBIN-19 plasmid. The resultant recombinants are referred to as pFG-1, pFG-2, pFG-3, pFG-14, pFG-18, pFG-19, pFG-22, and pFG-23. Using triparental mating technique, pBIN-19 plasmids containing the binary expression cassettes of genes were transferred from *E coli* DH5α to the LBA 4404 strain of *Agrobacterium tumefaciens* via a helper *E. coli* bacteria containing the RK 2013 plasmid. The transformed agrobacteria were selected using Minimal T medium (50 ml/L of 20 g/L $NH_4Cl$, 4 g/L $MgSO_4$-$7H_2O$, 0.06 g/L $MnCl_2$-$4H_2O$, 0.02 g/L $CaCl_2$, 0.1 g/L $FeSO_4$-$7H_2O$, 210 g/L $K_2HPO_4$, 90 g/L $KH_2PO_4$, 5 g/L sucrose and 16 g/L bactoagar) supplemented with 100 μg/mL kanamycin sulfate. Transformants were verified through DNA restriction analysis of the binary plasmid, and were maintained for leaf-disc transformation of tobacco.

Leaves were selected from axenic tobacco plantlets, trimmed to remove the mid-rib and leaf margins, and cut into discs of 0.5–1 cm size. The leaf-discs were soaked briefly in medium containing log-phase gown transformed agrobacteria, blotted clean on sterile filter paper, and then placed upside down on the surface of tobacco feeder-cell plate medium (100 ml W38 solid medium comprising 4.3.g/L MS medium powder (Gibco), 30 g/L sucrose, 0.1 g/L myo-inositol, 1 ml/L thiamine-HCl stock (0.4 mg/ml) 1 ml/L 6-benzylaminopurine stock (0.1 mg/ml), 3 ml/L 1-napthaleneacetic acid (1 mg/L) and 8 g/L low melting point agarose, pH 5.8). Agrobacteria co-cultivation was continued for 3 days in a growth chamber at 25° C. with continuous illumination (2000 lux). The co-cultivated leaf-discs were transferred to tobacco shooting medium (4.3.g/L MS medium powder, 30 g/L sucrose, 9 ml/L 6-benzylaminopurine stock, 0.09 ml/L 1-napthaleneacetic acid, 1 ml/L B-5 vitamin stock and 8 g/L phytoagar, pH 5.8) supplemented with 200 μg/mL kanamycin sulfate and 500 μg/mL carbenicillin. The leaf-discs were transferred to the same fresh medium every seven days until calli emerge and grow into size of 0.4 cm or more in diameter. When the shoots reached about 1 cm in length, they were excised from calli and transplanted into solid MS medium containing 100 ug/ml kanamycin sulfate.

Example 6

This example describes detection of GUS, IBVM-GUS, and IBV-m1Δ-GUS protein in transformed tobacco plant samples by Western blot.

Leaf microsomes were isolated according to the method described in Example 5 from a non-transgenic plant (Control), an IBVM-GUS transgenic plant with the heat-shock promoter (pFG 13-8), an IBVM-GUS transgenic plant with the CaM V 35S—35S promoter (pFG 14-23), an IBV-m1Δ-GUS transgenic plant with the CaM V 35S—35S promoter (pFG 22-41), Gm-1 transgenic plant with CaM V 35S—35S promoter (pFG 23-7), a GUS transgenic plant (pBI-121), VSVG transgenic plants expressing VSVG, VSVG-TA2, VSVG-TA1 and VSVG-TA1,2 (pFG-5, pFG-1, pFG-2 and pFG-3) and SYNVG transgenic plants (pFG 18-23). Heat treatment of leaves was conducted at 42° C. for 2 hours in a water bath, followed by incubation at 22° C. for 20 hours prior to homogenization of leaves. Proteins were extracted from microsomes using 1× extraction buffer for use in a GUS assay. The native GUS from the pBI-121 plant was concentrated from the supernatant of the leaf homogenate using an Amicon Centricon P-30. Protein (40 μg to 200 μg, depending upon the sample) samples were subjected to SDS-PAGE gel electrophoresis (4% stacking gel, 7.5% running gel). Following transfer of the protein from the gel to a blot, the blot was incubated with the appropriate antibodies depending upon the protein to be detected using the antibodies and methods described in Example 3. GUS proteins were identified using a preabsorbed polyclonal rabbit anti-GUS antibody at a 1:1,000 dilution (Molecular Probe, Eugene, Oreg.) and goat anti-rabbit IgG (H+L) alkaline phosphatase conjugate at a 1:10,000 (Sigma, St. Louis, Mo.).

Immunoreactive protein having a molecular weight of about 95 kD was observed in all the extracts from the transgenic plants expressing IBVM-GUS. Two bands having molecular weights of 95 kD and 92 kD were observed in samples containing IBVM-GUS protein encoded by expression vectors regulated by a CaM V double 35S promoter. A single 95 kD band, of lesser intensity, was seen in the extracts from the transgenic plant in which IBVM-GUS chimeric protein expression was regulated by a heat shock promoter. Two bands of the -m1Δ-GUS chimeric protein were observed having molecular weights of about 77 kD. The smaller bands of IBVM-GUS and IBV-m1Δ-GUS may be products of proteolysis.

Transgenic plants expressing the Gm-1 chimeric protein showed a pattern similar to that observed in transfected protoplasts. The molecular sizes of two isoforms were estimated at about 61 kD and 52 kD. The smaller isoform showed lesser intensity, but a more diffusive pattern, than the larger isoform.

Transgenic plants expressing VSVG and its mutants (pFG 1, pFG 2 and pFG 3) displayed two isoforms having molecular weights of about 61 kD and 52 kD. The band intensities of the smaller isoform were diffusive and less intense than the larger isoform.

The percentage of plants expressing the transformed plasmids are summarized in Table 2.

TABLE 2

Identified positive transformants and their percentage (%) in the screened population

| Binary Vectors for Transformation | Total Transformants Screened | Positive Transformants | Percentage (%) of Positive Plants |
|---|---|---|---|
| pFG 19 | 23 | NA | NA |
| pFG 14 | 19 | 17 (15) | 89.5 |
| pFG 13 | 17 | 13 (12) | 76.5 |
| pFG 22 | 20 | 14 (10) | 70.0 |
| pFG 23 | 11 | 6 (4) | 54.5 |
| pFG 1 | 3 | 1 | 33.3 |
| pFG 2 | 3 | 2 | 66.7 |
| pFG 3 | 2 | 1 | 50.0 |
| pFG 18 | 24 | 11 (5) | 45.8 |

Note: The number in the parenthesis indicates the plants that highly express the engineered genes.

With the exception of the transgenic plants containing the pFG-19 cassette, all transformed plants expressed the appropriate protein when analyzed using the appropriate antibodies.

Example 7

This Example describes the subcellular distribution of IBVM-GUS and Gm-1 in tobacco leaf protoplasts.

A. IBVM-GUS Distribution

Viable protoplasts transformed with plasmid encoding GUS, IBVM-GUS and IBV-m1Δ-GUS were lysed in ice-cold HBST medium 20 hours after transformation by several passages through a 26 gauge, one-half inch hypodermic syringe needle. All further procedures were conducted at 4° C. unless analyses required different temperatures. Lysed protoplasts in HBST medium were subject to two rounds of centrifugation. The first round was at 1000 g for 20 min. to pellet nuclei and heavy debris, designated as nuclei. The supernatant was subjected to further centrifugation at 300,000 g for 60 minutes in a Beckman TL-100 Ultrafuge (Beckman, Fullerton, Calif.) to separate membranes from the cytosolic fraction, designated respectively as microsomes and cytoplasm.

Protein concentrations and specific GUS activities were measured for each fraction using the methods described in example 2. Percentage of GUS activity in each fraction was calculated as a proportion of total GUS activities in each treatment. About 70% of the GUS activity of protoplasts transfected with the IBVM-GUS encoding plasmid (pFG-11A) was located in the endomembrane fraction, whereas 99% of the GUS activity was found in the cytosolic fraction of protoplasts transfected with the wild type GUS plasmid (pBAP-15). From about 20% to about 25% of the total GUS activity was always detected in the cytoplasmic fractions in protoplasts expressing IBVM-GUS (pFG-11A) and IBV-m1Δ-GUS (pFG-20.

B. Gm-1 Distribution

Protoplasts transformed with plasmid encoding Gm-1 protein (pFG-21) were subfractionated and analyzed by Western blot according to the method described in Example 2. In brief, the cytosolic fraction was concentrated through an Amicon Centricon P-30 and mixed with an equal volume of 2× SDS-sample buffer. The resuspended nuclear and microsomal fractions (equivalent to 4×10$^5$ protoplasts) were directly mixed with an equal volume of 2× SDS-sample buffer. The samples were resolved on a 7.5% SDS-PAGE gel. Resultant blots were incubated with preabsorbed polyclonal rabbit anti-VSV serum (1:2,500) and Goat anti-rabbit IgG (H+L) alkaline phosphatase conjugate (1:10,000). The larger isoform of Gm-1 was predominantly present in the microsomal fraction, with a lesser amount in the nuclear/heavy membrane fraction. The larger isoform (61 kD) was not found in the soluble cytoplasmic fraction. The smaller isoform (52 kD) was observed in all three subcellular fractions, indicating that a certain amount of the smaller isoform was released from membranes into the cytoplasm. The majority of the 52 kD protein was associated with the microsomal fraction. The association of Gm-1 with nuclear fraction is due to the fact that the outer nuclear membrane form a continuum with the rough ER.

Example 8

This example describes the confirmation that IBVM-GUS protein is bound to microsomal membranes.

Microsomes were isolated from leaf homogenates derived from plants transformed with IBVM-GUS encoding plasmid (pFG-14), non-transformed plants and plants expressing native GUS. Microsomes were isolated by differential centrifugation at 200 g for 20 min. and 300,000 g for 60 min. at 4° C. of tobacco leaf homogenates. About 2 mg of microsomal proteins were incubated in HBST (Meyer et al., 1988; 50 mM Tris, 1 mM EDTA, 300 mM sucrose, 1 mM PMSF, 5 mM ascorbic acid, 3.6 mM cysteine and 100 µg/mL BHT, pH 8.0) medium or HBST medium containing 0.4M NaCl and 1% Triton X-100 for 30 min. at 22° C. The microsomal proteins were centrifuged at 300,000 g for 60 min. at 4° C. to separate the microsomes from the incubation medium. Each fraction was assayed for GUS activity using the method described in Example 4. A 100% GUS activity distribution was detected in the microsomal fraction from samples not treated with 1% Triton X-100 as in the supernatant fraction from samples that were treated with 1% Triton X-100.

Fractionation of GUS activity with the microsomal fraction when treated with buffer without salt and detergent indicates that the recombinant IBVM-GUS chimeric protein is membrane-bound. The membrane-bound chimeric protein is released upon exposure to the detergent contained in the HBST salt buffer.

Example 9

This Example describes the localization of IBVM-GUS chimeric proteins to a cellular compartment by measuring GUS activity in fractionated transformed tobacco plant cell membranes.

About 10$^6$ viable protoplasts were purified from tobacco leaves transformed with pFG-11A plasmid (IBVM-GUS) or pBAP-15 plasmid 8, 12, 16.7 and 24 hours after transformation. The protoplasts were isolated using the method of Example 2. The protoplasts were then lysed in ice-cold HBST medium. The lysates were centrifuged at 200 g for 20 min. at 4° C., the supernatant collected and adjusted to a sucrose concentration of 10–12% w/w and loaded onto a 20–50% linear sucrose gradient (buffered with 10 mM tris and 1 mM EDTA, pH 8.0). After centrifugation at 240,000 g for 18 hours at 4° C. and the gradient fractionated into 20 0.6 mL fractions.

The chlorophyll content (arbitrary fluorescence units/0.05 mL fraction) in the fractions was measured immediately after fractionation according to the method described by Galbraith et al. (*Planta* 186:324–336, 1992).

The antimycin A insensitive NADH cytochrome c reductase ($\Delta A_{550}/4$ min/mL fraction) in the fractions was measured using the protocol described by Donaldson et al. (*Arc. Biochem. Biophy.* 152:199–215, 1972).

The activity of GUS in the fractions was measured immediately after fractionation using the method disclosed in Example 4.

The latent IDPase activity in the fractions was measured 2–3 days after storage at −80° C. using the protocol described by Gardiner et al. (*Plant Physiol.* 55:536–541, 1975).

The vanadate-sensitive ATPase (($\Delta A_{710}/4$ min/mL fraction) in the fractions was measured 2–3 days after storage at −80° C. using the protocol as described by Briskin et al. (*Method Enzymol.* 148:542–559, 1987).

When analyzed 24 hours after transformation, the distribution of the membranes carrying GUS activity (see FIG. 5C) were distinct from those containing chlorophyll (see FIG. 5A), NADH cytochrome c reductase (FIG. 5B) and vanadate-sensitive ATPase (FIG. 5E) but overlapped with the membranes carrying latent inosine diphosphatase (IDPase) activity. Since IDPase is a plant Golgi marker enzyme, this result indicates that the GUS activity is present in the Golgi of the tobacco cells.

Figure 5:
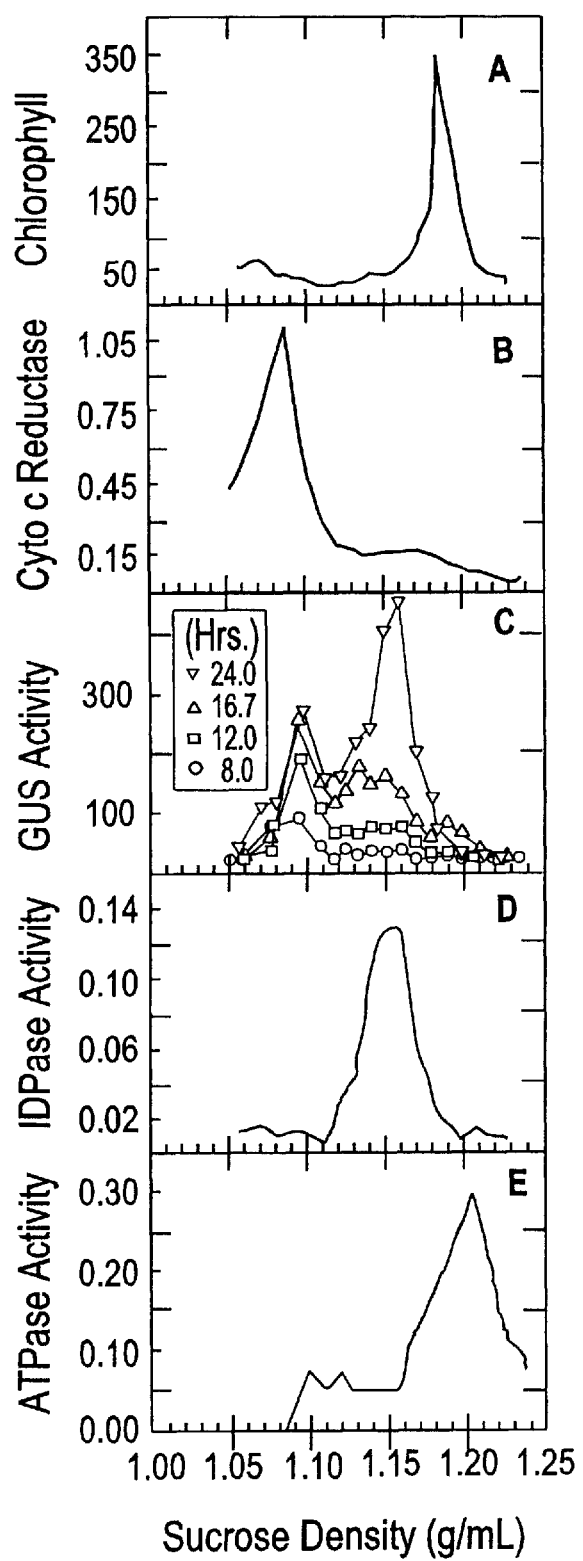
FIGS. 5A–5E illustrate the results of sucrose density gradients of protoplasts correlated with various enzymatic functions.

As a function of time after transformation, GUS activity was first detected in the membranes of the endoplasmic reticulum at about 16.7 hours (see FIG. 5C). At subsequent time points, there was a progressive accumulation of GUS activity in association with the membrane fractions having higher densities. The position of the heavier membrane fractions was similar to that of the Golgi membrane fraction in the sucrose gradient. As incubation periods were increased, the accumulation of GUS activity within the heavier membrane fractions were progressively shifted toward a lower position in the sucrose gradient, but not as far as the position of the plasma membrane fraction. The foregoing pattern is consistent with the conclusion that the recombinant IBVM-GUS protein is first synthesized on the polyribosomes of the ER, is partially translocated across the ER and finally accumulates within a membrane compartment having a higher density than the ER.

Results

Taken together, the results from Examples 1–9 indicate that IBVM-GUS, VSVG and SYNVG encoding plasmids can be expressed in tobacco leaf protoplasts and tobacco plants. The recombinant proteins have the correct molecular weight as predicted from the nucleic acid sequence. In addition, the recombinant IBVM-GUS chimeric protein has active β-Glucuronidase activity.

Native GUS expressed in transgenic plants is cytoplasmically located. The first transmembrane domain of M contains a retention and accumulation sequence for the cis Golgi. Expression of the IBVM-GUS chimeric protein can be readily detected in either transformed protoplasts or plants by Western blot or β-Glucuronidase activity. In particular, the recombinant chimeric protein is detected in the endomembrane-secretory pathway of the plant cells. Furthermore, the chimeric protein isolated from tobacco leaves was determined to be membrane-bound.

Thus, the results indicate that IBVM-GUS chimeric protein expressed in tobacco leaves is bound to a membrane located in the endomembrane-secretory pathway of tobacco cells where the protein remains intact such that the protein maintains its immunoreactivity and GUS activity.

Example 10

This example describes the morphological analysis of cultured cells expressing IBVM-GUS chimeric protein by electron microscopy.

Suspension cells from tobacco plants transformed with pFG-14-23 plasmid were prepared for electron microscopy as follows. Cell cultures were allowed to settle in tubes and the culture medium removed. The cells were resuspended in 0.2 M sorbitol and 0.5% (w/v) low temperature-melting agarose (Type IX, Sigma, St. Louis, Mo.) and centrifuged at 1,000 g for 1 min. Aliquots of the cell slurry were transferred to specimen carriers and cryofixed in a Balzers HPM 010 high pressure freezing apparatus (BAL-TEC Products Inc., Middlebury, Calif.), freeze-substituted in 2% osmium tetraoxide in acetone at −80° C. for 3 days and then warmed to −20° C., 4° C. and room temperature for 2 hours each. After rinsing in acetone, the samples were embedded in Epon-Araldite resin. Thin sections were stained with uranyl acetate and lead citrate. The sections were then visualized using a Philips CM10 transmission electron microscope (Philips Electronic Instruments, Mahwah, N.J.) and a JEOL 100C electron microscope (JEOL USA Inc., Peebody, Mass.).

The resulting electron micrographs are shown in FIGS. 4A–4D. Culture cells expressing the IBVM-GUS chimeric protein exhibited novel membranous proliferations that were not observed in untransformed cells. These membranous proliferations are continuous with, and are derived from, the cisternae of the ER. The membranous proliferations appear as either parallel membrane sheets or as stacked "whorl-like" structures consisting of tightly wrapped cisternae in a concentric or spirillal configuration. Densely stained material is associated with the cytoplasmic surfaces of the appressed membranes. Lumenal spaces are comparable in width and staining to those of a conventional ER. The number of cisternae wrapped in whorls or organized as concentric layers or membrane stacks varied from about 2 to about 10 and the overall diameter of the whorls typically ranged from between about 1.0 μm to about 3 μm.

The foregoing observations indicate that the presence of recombinant IBVM-GUS chimeric proteins in plant cells results in the formation of novel membrane compartments having distinct morphological configurations.

Example 11

This example describes the immunolabelling of cultured cells expressing IBVM-GUS chimeric protein for analysis by electron microscopy.

Thin sections were prepared as described in Example 10. The sections were mounted on formvar-coated nickel grids and treated with sodium metaperiodate for 10 min., rinsed in water, blocked with 0.1% fish gelatin (Jansen Pharmaceuticals, Piscataway, N.J.) and 0.8% bovine serum albumin in PBST (10 mM sodium phosphate, pH 7.2, 250 mM NaCl, 0.1% Tween 20) for 15 min, labelled with rabbit anti-GUS antibody (described in Example 3) for 2 hours, rinsed in PBST and labelled with protein A-colloidal gold conjugate (BioCell Research Laboratories) diluted at 1:20 in blocking solution. The stained sections were then visualized using the transmission electron microscopes described above.

Electron dense particles representing colloidal gold immunostaining of GUS protein were associated with the densely staining material at the cytoplasmic interface of the adhering whorl-like membrane cisternae described in Example 10. The localization of GUS staining is consistent with the predicted orientation of the IBVM-GUS chimeric protein, in which the GUS protein is exposed to the cytoplasmic surface of the ER cisternae, thus causing the production of stacked whorl-like membrane structures rather than planar membrane structures (see FIG. 4C). Neither the non-appressed, conventional rough ER, smooth ER nor Golgi stacks exhibited immunolabelling, thus indicating that essentially all of the IBVM-GUS chimeric protein was localized in the whorl-like structures. This localization permits the non-altered ER and Golgi apparatus of the cell to continue to function normally.

Example 12

This example describes the immunofluorescence labelling of cells transformed with IBVM-GUS encoding plasmid.

Cultured cells transformed with pFG-14-23 plasmid were cultured for 6 days. The cells were then fixed with 2% paraformaldehyde in K-medium (described in Galbraith et al., *Proc. Natl. Acad. of Sci.*, 87:816, 1990) for 1 hour. After thorough rinsing with K-medium, the cells were treated with 1% cellulysin cellulase and 0.2% macerase pectinase (Calbiochem, La Jolla, Calif.) in K-medium for about 2 hours at 25° C. The cells were rinsed again and then permeabilized in TSW medium (Galbraith et al., ibid.) for 30 min. and then rinsed in TSW medium without SDS. The primary antiserum containing anti-GUS antibodies was pre-absorbed for 1 hour on non-fixed cells. Permeabilized cells were incubated in the preabsorbed anti-Gus antibodies at a concentration of 1:100 for 3 hours. The cells were then rinsed in TSW medium without SDS. Fluorescein conjugated goat anti-rabbit IgG (Jackson ImmunoResearch, West Grove, Pa.) was added to the cells at a dilution of 1:200 and the cells were incubated for 1 hour in darkness at room temperature. After rinsing, the cells were viewed with a Zeiss Axioskop fluorescence microscope.

Numerous bright fluorescence spots were observed throughout the cytoplasm of the stained cells. The staining represents the membranous proliferations described in Example 10 because the size and distribution of the fluorescent spots matched the size and distribution of the whorl-like structures observed by electron microscopy. Based upon the number of fluorescent spots observed, the average transformed suspension of cells contains about 20 to about 50 membranous proliferations.

Results

Taken together, the results described in Examples 10–12 indicate that the expression of plasmids encoding IBVM-GUS chimeric protein results in the formation of novel membranous proliferations. Based on the morphology of the membranous proliferations and the ability of GUS molecules to form tetrameric homo-oligomers, the GUS domains of the IBVM-GUS chimeric proteins that is located on the cytoplasmic side of the ER membrane are forming oligomers between GUS molecules, thereby causing the ER membrane to become zippered together into concentric circles or parallel sheets. The formation of GUS oligomers is supported by the results obtained in Example 9 indicating substantial GUS activity within the ER membrane-containing sucrose gradient fraction. The accumulation of substantial GUS activity in the ER membrane fraction also indicates that the IBVM-GUS chimeric proteins are protected from degradation by cellular proteases when localized within the whorl-like structures.

Example 13

This example describes the production and expression of gene constructs encoding GUS protein or GUS protein associated with IBVM transmembrane domains in yeast cells.

A. Preparation of Yeast Expression Vectors

The following expression vectors were used to create recombinant molecules containing GUS, IBVM or IBVM/GUS encoding nucleic acid sequences useful for expression in yeast cells. The expression vectors pNZ103a and YEp51, each contain a GAL10 galactose inducible promoter for high level expression of a desired gene. They also contain DNA encoding several different selectable markers including DNA that encodes for ampicillin resistance; the LEU2 gene in pNZ103a and the HIS3 gene in YEp51, that encode for a protein product that allows for selection on media lacking leucine or histidine, respectively. The vectors also contain a bacterial origin of replication and a 2$\mu$ origin of replication for high plasmid copy number in yeast. A third expression vector system consisting of two plasmids, pG-N795 and p2UG. pG-N795 contains the gene for a glucocorticoid receptor under control of the constitutive GPD (glyceraldehyde-3-phosphate dehydrogenase) promoter; a bacterial replication origin, an ampicillin resistance gene, a 2$\mu$ origin of replication and the TRP1 auxotrophic marker; p2UG contains three glucocorticoid responsive elements (GRE) fused to a yeast CYC1 promoter; a bacterial origin of replication; an ampicillin resistance gene; an origin of replication; and an URA3 auxotrophic marker. Use of a galactose inducible promoter results in an approximately 10-fold increase in expression over the glucocorticoid system.

The nucleic acid molecules encoding IBV-M/GUS fusion protein, IBV-M and GUS were isolated as described in Example 1. The IBV-M/GUS fusion protein encoding nucleic acid was subcloned into YEp51 vector and is referred to herein as IBVM/GUS-YEp51. The IBV-M nucleic acid molecule was subcloned into pNZ103a and is referred to herein as pNZ103a-IBVM. The GUS nucleic acid molecule was subcloned into both pNZ103a (referred to as GUS-pNZ) and p2UG (referred to as GUS-p2UG).

B. Transformation of Yeast

Yeast were transformed using the PLATE transformation method. Three large colonies of yeast were scraped from an agar plate and placed in 500 $\mu$l of a solution of 40% PEG-4000, 10 mM Tris-HCl [pH 7.5], 100 mM Lithium Acetate, 1 mM EDTA, and 0.2 mg/mL salmon sperm DNA. Four $\mu$l of expression vector was added to the cells and incubated overnight at room temperature. Fifty $\mu$l of transformed yeast which have settled to the bottom of the tube were then plated on selective agar plates and allowed to grow at 30° C. for approximately three days.

C. Growth of Yeast and Induction of Protein Expression

Five ml of a 2% raffinose solution (2% raffinose, 6.7 mg/L Yeast Nitrogen Base, amino acids) was inoculated with a colony of transformed yeast and allowed to grow with agitation overnight at 30° C. The culture was then used to inoculate a larger culture of yeast for high pressure freezing. Protein expression was induced for an appropriate amount of time with either 20% galactose for yeast cells transformed with YEp51 and pNZ103a expression vectors or 10 $\mu$M deoxycorticosterone for yeast cells transformed with p2UG expression vectors.

D. Analysis of Transformed Yeast by Electron Microscopy

Protein expression induced yeast cells were concentrated on 0.45 $\mu$m filters and high pressure frozen. The cells were freeze substituted in 20% $OsO_4$, 8% DMP in acetone for 72 hours and then slowly warmed to room temperature over 6 hours. Samples were then placed in 0.5% uranyl acetate in acetone for two hours at room temperature and then overnight at 4° C. Samples were slowly embedded in Spurrs resin and hardened at 70° C. Thin sections of yeast cells were cut using a microtome, placed on Formvar coated grids and stained for 5 minutes with 0.5% uranyl acetate in water and 3 minutes with lead citrate in water. Samples were visualized on a Philips CM10 electron microscope.

A representative view of a cross-section of a yeast cell transformed with IBVM/GUS is shown in FIG. 4E.

E. Analysis of Transformed Yeast by Immunolabelling and Electron Microscopy

Yeast cells transformed with IBVM/GUS were prepared as described above in Section D. The grids were incubated with anti-GUS antibody bound to colloidal gold. A representative immunolabelled yeast cell cross-section is shown in FIG. 4F.

Results

Taken together, the results described in Examples 10–13 indicate that the expression of plasmids encoding IBVM-GUS chimeric protein results in the formation of novel membranous proliferations in both plant cells and yeast cells. Based on the morphology of the membranous proliferations and the ability of GUS molecules to form tetrameric homo-oligomers, the GUS domains of the IBVM-GUS chimeric proteins that is located on the cytoplasmic side of the ER membrane are forming oligomers between GUS molecules, thereby causing the ER membrane to become zippered together into parallel sheets. The formation of GUS oligomers is supported by the results obtained in Example 10 indicating substantial GUS activity within the ER membrane-containing sucrose gradient fraction. The accumulation of substantial GUS activity in the ER membrane fraction also indicates that the IBVM-GUS chimeric proteins are protected from degradation by cellular proteases when localized within the parallel sheet structures.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed:

1. A method to aggregate a desired product molecule in a lipid bilayer, comprising forming oligomers between two or more aggregate molecules that are physically associated with a lipid bilayer such that said aggregate molecules are accumulated in association with said lipid bilayer, wherein said aggregate molecules comprise a β-glucuronidase (GUS) adhesive molecule, and wherein said desired product molecule is linked to said adhesive molecule by a transmembrane molecule.

2. The method of claim 1, wherein a sufficient number of said aggregate molecules are used to generate at least one membrane compartment having a morphology substantially similar to one or more membrane compartments shown in FIG. 4.

3. The method of claim 1, wherein said step of aggregating is performed in a live cell.

4. The method of claim 1, wherein said step of aggregating does not substantially interfere with cellular function.

5. The method of claim 1, wherein said aggregate molecule has a molecular weight more than the molecular weight of GUS.

6. The method of claim 1, wherein said aggregate molecules have a molecular weight of about 73 kD.

7. The method of claim 1, wherein said aggregate molecules comprise at least a portion of a second adhesive molecule that forms an oligomer, said second adhesive molecule being selected from the group consisting of β-glucuronidase, a lectin, biotin, avidin, T4 phage coat protein, T4 phage tail protein, hemoglobin and immunoglobin.

8. The method of claim 1, wherein said aggregate molecules comprise a full-length GUS.

9. The method of claim 1, wherein said desired product molecule is selected from the group consisting of a secreted protein and an intracellular protein.

10. The method of claim 1, wherein said transmembrane molecule comprises a transmembrane domain of said desired product molecule.

11. The method of claim 1, wherein said transmembrane molecule comprises a protein having from 1 to 12 membrane-spanning domains.

12. The method of claim 1, wherein said transmembrane molecule comprises a protein having from 1 to 6 membrane-spanning domains.

13. The method of claim 1, wherein said transmembrane molecule comprises a protein having from 3 membrane-spanning domains.

14. The method of claim 1, wherein said aggregate molecule comprises a transmembrane molecule from a protein selected from the group consisting of coronavirus avian infectious bronchitis virus M protein, cytochrome b6, light harvesting complex protein, early light induced protein of chloroplast, VSV-G, glycophorin, sodium-potassium ATP'ase subunit, glycosyl transferase, mannosidase-2, lamin B receptor, immunoglobulin, viral envelope protein, an enzyme that regulates lipid production, an enzyme that regulates steroid production, an anti-thrombin molecule, an antigen, a toleragen, a cytokine and a toxin.

15. The method of claim 1, wherein said transmembrane molecule comprises at least a portion of a coronavirus avian infectious bronchitis virus M protein.

16. The method of claim 1, wherein said aggregate molecule further comprises a proteolytic restriction site.

17. The method of claim 1, wherein said aggregate molecule further comprises a restriction protease sequence which is cleaved by a restriction protease selected from the group consisting of collagenases, serine proteases, metalloproteases, aspartic acid proteases and cysteine proteases.

18. The method of claim 1, wherein said lipid bilayer is a eukaryotic cell membrane.

19. The method of claim 1, wherein said lipid bilayer is selected from the group consisting of a fungal membrane, a protozoan membrane, an algal membrane, an amoeboid membrane, a yeast membrane, an animal membrane and a plant membrane.

20. The method of claim 1, wherein said lipid bilayer is selected from the group consisting of an outer cell membrane, an inner cell membrane and an organelle membrane.

21. The method of claim 20, wherein said organelle membrane is selected from the group consisting of a plasma membrane, an endocytic vesicle membrane, a lysosomal vesicle membrane, a secretory vesicle membrane, a transport vesicle membrane, an endosomal membrane system, a mitochondria membrane, an endoplasmic reticulum membrane, nuclear envelope membrane, a Golgi apparatus membrane, a trans-Golgi network membrane, a cis-Golgi network membrane, a yeast cell vacuole membrane, a plastid, a peroxisome membrane, and different collections thereof.

22. The method of claim 1, wherein said lipid bilayer is selected from the group consisting of an endoplasmic reticulum and a nuclear envelope membrane.

23. The method of claim 1, further comprising expressing in a cell at least one nucleic acid molecule encoding said aggregate molecule.

24. The method of claim 23, wherein said cell is selected from the group consisting of an insect cell, a fungal cell, a protozoan, an algae, an amoeba, a yeast membrane, an animal cell and a plant cell.

25. The method of claim 23, wherein said cell is selected from the group consisting of a plant cell, an animal cell and a yeast cell.

26. The method of claim 23, wherein said nucleic acid molecule is operatively linked to an expression vector to form a recombinant molecule.

27. The method of claim 26, wherein said expression vector comprises a CaMV35S promoter and a CaMV35S polyadenylation sequence.

28. The method of claim 1, wherein said step of aggregating comprises accumulating said aggregate molecule in a portion of a membrane compartment.

29. The method of claim 28, wherein said membrane compartment is selected from the group consisting of a cell and an organelle.

30. The method of claim 29, wherein said organelle is selected from the group consisting of a plasma membrane, an endocytic vesicle membrane, a lysosomal vesicle membrane, a secretory vesicle membrane, a transport vesicle membrane, an endosomal membrane system, a mitochondria membrane, an endoplasmic reticulum membrane, nuclear envelope membrane, a Golgi apparatus membrane, a trans-Golgi network membrane, a cis-Golgi network membrane, a yeast cell vacuole membrane, a plastid, a peroxisome membrane, and different collections thereof.

31. The method of claim 1, wherein said step of aggregating results in the formation of a non-naturally occurring membrane housing compartment.

32. A non-naturally occurring membrane housing compartment contained within a cell inside of which aggregate proteins are sequestered without substantially interfering with cellular function, wherein said membrane housing compartment is selected from the group consisting of a portion of an endoplasmic reticulum and a portion of an outer nuclear envelope membrane, and wherein said aggregate proteins comprise a GUS adhesive molecule and a transmembrane molecule which anchors said aggregate proteins to said membrane housing compartment.

33. The membrane housing compartment of claim 32, wherein said membrane housing compartment is selected from the group consisting of stacked membrane structures and planar membrane structures.

34. The membrane housing compartment of claim 32, wherein said membrane housing compartment is formed by forming oligomers between a sufficient number of aggregate molecules such that a membrane compartment is formed that is substantially similar to the morphology of one or more membrane compartments shown in FIG. 4.

35. The membrane housing compartment of claim 32, wherein said aggregate molecule further comprises a second adhesive molecule comprising at least a portion of a protein selected from the group consisting of β-glucuronidase, a lectin, biotin, avidin, T4 phage coat protein, T4 phage tail protein, hemoglobin and immunoglobulin.

36. The membrane housing compartment of claim 32, wherein said aggregate proteins comprise a full-length GUS.

37. The membrane housing compartment of claim 32, wherein said aggregate proteins comprise a transmembrane molecule from a protein selected from the group consisting of coronavirus avian infectious bronchitis virus M protein, cytochrome b6, light harvesting complex protein, early light induced protein of chloroplast, VSV-G, glycophorin, sodium-potassium ATP'ase subunit, glycosyl transferase, mannosidase-2, lamin B receptor, immunoglobulin, viral envelope protein, an enzyme that regulates lipid production, an enzyme that regulates steroid production, an antithrombin molecule, an antigen, a toleragen, a cytokine and a toxin.

38. A nucleic acid molecule encoding an aggregate molecule comprising:

a) a GUS adhesive molecule which forms oligomers between two or more aggregate molecules, said adhesive molecule attached to a transmembrane molecule; and b) a desired product molecule functionally associated with said adhesive molecule.

39. The nucleic acid molecule of claim 38, wherein said aggregate molecule comprises a full-length GUS.

40. The nucleic acid molecule of claim 38, wherein said transmembrane molecule comprises at least a portion of a coronavirus avian infectious bronchitis virus M protein.

41. The nucleic acid molecule of claim 38, wherein said nucleic acid molecule is covalently associated with a nucleic acid molecule encoding a signal sequence.

42. The nucleic acid molecule of claim 38, wherein said nucleic acid molecule is operatively linked to an expression vector to form a recombinant molecule.

43. The nucleic acid molecule of claim 42, wherein said expression vector comprises a CaMV35S promoter and a CaMV35S polyadenylation sequence.

44. A recombinant cell having a recombinant molecule comprising a nucleic acid molecule operatively linked to an expression vector, said nucleic acid molecule encoding an aggregate molecule comprising a GUS adhesive molecule which physically associates with a lipid bilayer in such a manner that said aggregate molecule is accumulated in association with a portion of said lipid bilayer upon expression of said recombinant molecule in said recombinant cell, wherein said aggregate molecule is linked to said lipid bilayer by a transmembrane molecule.

45. The recombinant cell of claim 44, wherein said accumulation of said aggregate molecule does not substantially interfere with the function of said recombinant cell.

46. The recombinant cell of claim 44, wherein said recombinant molecule further comprises a nucleic acid sequence encoding a desired product molecule functionally associated with said adhesive molecule.

47. The recombinant cell of claim 44, wherein said recombinant cell is derived from a host cell selected from the group consisting of a plant cell, an animal cell, a fungal cell, a yeast cell, an insect cell, an algal cell, an amoeboid cell and a protozoan cell.

48. A method for increasing the concentration of a desired product molecule within a cell, comprising forming within a cell oligomers between two or more aggregate molecules having desired product molecules attached thereto, wherein the concentration of said desired product molecules in said cell exceeds the concentration of said desired product molecules in cells where said oligomers are not formed, wherein said aggregate molecules comprise a GUS adhesive molecule, and wherein said desired product molecule is linked to said aggregate molecules by a transmembrane molecule.

49. The method of claim 48, wherein said concentration of said desired product molecule in said cell in which said oligomers have formed is at least about 2-fold higher than said concentration of said desired product molecule in said cell in which no said oligomers have formed.

50. A plant cell comprising a non-naturally occurring membrane housing compartment inside of which aggregate proteins are sequestered without substantially interfering with cellular function, wherein said aggregate proteins comprise a GUS adhesive molecule which forms oligomers between two or more of said aggregate molecules and said adhesive molecule is linked to a desired product molecule by a transmembrane molecule.

* * * * *